United States Patent
Dieterle et al.

(10) Patent No.: US 7,524,792 B2
(45) Date of Patent: Apr. 28, 2009

(54) PREPARATION OF CATALYTICALLY ACTIVE MULTIELEMENT OXIDE MATERIALS WHICH CONTAIN AT LEAST ONE OF THE ELEMENTS NB AND W AND THE ELEMENTS MO, V AND CU

(75) Inventors: Martin Dieterle, Mannheim (DE); Hartmut Hibst, Schriesheim (DE); Wolfgang Juergen Poepel, Darmstadt (DE); Jochen Petzoldt, Mannheim (DE); Klaus Joachim Mueller-Engel, Stutensee (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 809 days.

(21) Appl. No.: 10/840,745

(22) Filed: May 7, 2004

(65) Prior Publication Data

US 2004/0249183 A1 Dec. 9, 2004

Related U.S. Application Data

(60) Provisional application No. 60/530,617, filed on Dec. 19, 2003, provisional application No. 60/475,488, filed on Jun. 4, 2003.

(30) Foreign Application Priority Data

Jun. 4, 2003 (DE) ............... 103 25 488
Dec. 19, 2003 (DE) ............... 103 60 058

(51) Int. Cl.
*B01J 23/00* (2006.01)
(52) U.S. Cl. ............... 502/311; 502/312; 502/318; 502/321

(58) Field of Classification Search ............... 502/311, 502/312, 318, 321
See application file for complete search history.

(56) References Cited

U.S. PATENT DOCUMENTS

| 4,111,983 | A | | 9/1978 | Kurtz et al. | |
|---|---|---|---|---|---|
| RE29,901 | E | * | 2/1979 | Wada et al. ............... | 502/179 |
| 4,289,654 | A | | 9/1981 | Bertolini et al. | |
| 4,356,114 | A | | 10/1982 | Kadowaki et al. | |
| 4,415,752 | A | * | 11/1983 | Decker et al. ............... | 562/534 |

(Continued)

FOREIGN PATENT DOCUMENTS

DE 31 19 586 C2 2/1982

(Continued)

OTHER PUBLICATIONS

Database WPI, Week 7512, Derwent Publ. Ltd., London GB AN 75-2002.

*Primary Examiner*—Cam N. Nguyen
(74) *Attorney, Agent, or Firm*—Oblon, Spivak, McClelland, Maier & Neustadt, P.C.

(57) ABSTRACT

Catalytically active multielement oxide materials which contain at least one of the elements Nb and W and the elements Mo, V and Cu are prepared by a process in which an intimate dry blend containing ammonium ions is prepared and said dry blend is subjected to a thermal treatment in an atmosphere having a low molecular oxygen content at elevated temperatures, a portion of the ammonium ions contained in the intimate dry blend being decomposed with liberation of ammonia and the oxygen content of the thermal treatment atmosphere being increased in the course of the thermal treatment.

21 Claims, 9 Drawing Sheets

U.S. PATENT DOCUMENTS

| | | | | |
|---|---|---|---|---|
| 4,521,618 A * | 6/1985 | Arntz et al. | | 562/535 |
| 4,925,823 A * | 5/1990 | Krabetz et al. | | 502/211 |
| 5,173,468 A * | 12/1992 | Boehning et al. | | 502/209 |
| 5,364,825 A * | 11/1994 | Neumann et al. | | 502/311 |
| 5,446,004 A * | 8/1995 | Tenten et al. | | 502/312 |
| 5,521,137 A * | 5/1996 | Martin et al. | | 502/311 |
| 5,569,636 A * | 10/1996 | Martin et al. | | 502/311 |
| 5,583,086 A * | 12/1996 | Tenten et al. | | 502/249 |
| 5,637,546 A | 6/1997 | Tenten et al. | | |
| 5,677,261 A | 10/1997 | Tenten et al. | | |
| 5,686,373 A | 11/1997 | Tenten et al. | | |
| 5,807,531 A * | 9/1998 | Hibst et al. | | 252/518.1 |
| 5,885,922 A * | 3/1999 | Hibst et al. | | 502/305 |
| 5,910,608 A | 6/1999 | Tenten et al. | | |
| 5,959,143 A * | 9/1999 | Sugi et al. | | 562/534 |
| 6,025,523 A * | 2/2000 | Hecquet et al. | | 562/535 |
| 6,124,499 A * | 9/2000 | Hibst et al. | | 562/535 |
| 6,169,214 B1 | 1/2001 | Tenten et al. | | |
| 6,184,173 B1 * | 2/2001 | Hibst et al. | | 502/300 |
| 6,252,122 B1 * | 6/2001 | Tenten et al. | | 568/475 |
| 6,429,332 B1 * | 8/2002 | Tanimoto et al. | | 562/532 |
| 6,545,177 B2 * | 4/2003 | Tanimoto et al. | | 562/535 |
| 6,563,000 B1 * | 5/2003 | Yunoki et al. | | 562/532 |
| 6,638,890 B2 * | 10/2003 | Tanimoto et al. | | 502/300 |
| 6,762,148 B2 * | 7/2004 | Ohishi et al. | | 502/318 |
| 6,780,816 B2 * | 8/2004 | Tanimoto et al. | | 502/300 |
| 6,797,839 B1 * | 9/2004 | Hibst et al. | | 562/532 |
| 6,867,163 B2 * | 3/2005 | Takezawa et al. | | 502/321 |
| 6,881,702 B2 * | 4/2005 | Arnold et al. | | 502/311 |
| 6,921,836 B1 * | 7/2005 | Hibst et al. | | 562/535 |
| 2003/0181761 A1 | 9/2003 | Unverricht et al. | | |

FOREIGN PATENT DOCUMENTS

| | | |
|---|---|---|
| DE | 198 15 281 A1 | 10/1999 |
| DE | 100 46 928 A1 | 4/2002 |
| EP | 0 113 156 | 7/1984 |
| EP | 0 668 104 A1 | 8/1995 |
| EP | 0 714 700 A2 | 6/1996 |
| JP | 49-97793 | 9/1974 |
| WO | WO 95/11081 | 4/1995 |

* cited by examiner

PREPARATION OF CATALYTICALLY ACTIVE MULTIELEMENT OXIDE MATERIALS WHICH CONTAIN AT LEAST ONE OF THE ELEMENTS NB AND W AND THE ELEMENTS MO, V AND CU

CROSS REFERENCE TO RELATED APPLICATIONS

This application claims priority to and incorporates by reference the following applications: U.S. Provisional Application No. 60/530,617, filed on Dec. 19, 2003; U.S. Provisional Application No. 60/475,488, filed on Jun. 4, 2003; German Patent Application No. 103 25 488.9, filed on Jun. 4, 2003, and German Patent Application 103 60 058.2, filed on Dec. 19, 2003.

BACKGROUND OF THE INVENTION

1. Field of the Invention

The present invention relates to a process for the preparation of catalytically active multielement oxide materials which contain at least one of the elements Nb, W and the elements Mo, V and Cu, the molar fraction of the element Mo, based on the total amount of all elements of the catalytically active multielement oxide material, other than oxygen, being from 20 to 80 mol %, the molar ratio of Mo contained in the catalytically active multielement oxide material to V, Mo/V contained in the catalytically active multielement oxide material being from 15:1 to 1:1, the corresponding molar ratio Mo/Cu being from 30:1 to 1:3 and the corresponding molar ratio Mo/(total amount of W and Nb) being 80:1 to 1:4, in which an intimate dry blend also containing ammonium ions is prepared from starting compounds which contain the elemental constituents of the multielement oxide material, other than oxygen, as components and said dry blend is thermally treated in an atmosphere having a low content of molecular oxygen at elevated temperatures, at least a portion of the ammonium ions contained in the intimate dry blend being decomposed at $\geq 160°$ C. with liberation of ammonia.

The present invention also relates to a process for the preparation of acrylic acid by heterogeneously catalyzed partial gas-phase oxidation of acrolein using catalysts which contain the abovementioned multielement oxide materials as catalytically active materials.

The process, described at the outset, for the preparation of catalytically active multielement oxide materials is known, as is the use of the multielement oxide materials obtainable thereby as active material in catalysts for the heterogeneously catalyzed partial gas-phase oxidation of acrolein to acrylic acid.

2. Discussion of the Background

DE-31 19 586 C2 discloses that a catalytically active multielement oxide material which contains the elements Mo and V as base component can be prepared by preparing an intimate dry blend comprising ammonium ions from starting compounds which contain the elemental constituents or the multielement oxide materials as components, and thermally treating said dry blend at 380° C. in a gas stream which contains 1% by volume of molecular oxygen.

The resulting multielement oxides are recommended as active material for catalysts for the catalytic partial gas-phase oxidation of acrolein to acrylic acid.

DATABASE WPI, Week 7512, Derwent Publication Ltd., London, UK; AN 75-20002 & JP-A 49097793 (Asahi Chemical Ind. Co.), Sep. 19, 1974, recommends the thermal treatment of corresponding intimate dry blends for the preparation of relevant multielement oxide active materials with compete exclusion of molecular oxygen. EP-A 113 156 recommends carrying out the thermal treatment in an air stream. EP-A 724481 states that the thermal treatment should be carried out in such a way that the content of molecular oxygen at any point during the thermal treatment in the (gaseous) treatment atmosphere is from 0.5 to 4% by volume. In the exemplary embodiment, the molecular oxygen content in the thermal treatment atmosphere was 1.5% by volume.

In the exemplary embodiments of EP-A 714700, the thermal treatment of the intimate dry blend is carried out both in an air stream and in an atmosphere whose molecular oxygen content was 1.5% by volume.

DE-A 10046928, DE-A 19815281 and EP-A 668104 show that multielement oxide active materials which are mentioned at the outset and have a multiphase structure are particularly suitable as active materials for catalysts for the heterogeneously catalyzed partial oxidation of acrolein to acrylic acid when at least one phase is separately preformed for the preparation of the intimate dry blend to be thermally treated and the thermal treatment is carried out in a gas atmosphere which continuously contains from 1.5 to 1.4% by volume of molecular oxygen.

A disadvantage of the prior art is that substantially all of it recommends a thermal treatment of the intimate dry blend at a content of molecular oxygen which is substantially constant over the duration of the thermal treatment in the associated gas atmosphere.

However, relevant multielement oxide active materials obtained in this manner are not completely satisfactory with regard to activity and selectivity when used as active materials in catalysts for the heterogeneously catalyzed partial oxidation of acrolein to acrylic acid.

DETAILED DESCRIPTION OF THE PREFERRED EMBODIMENTS

Figure 1:
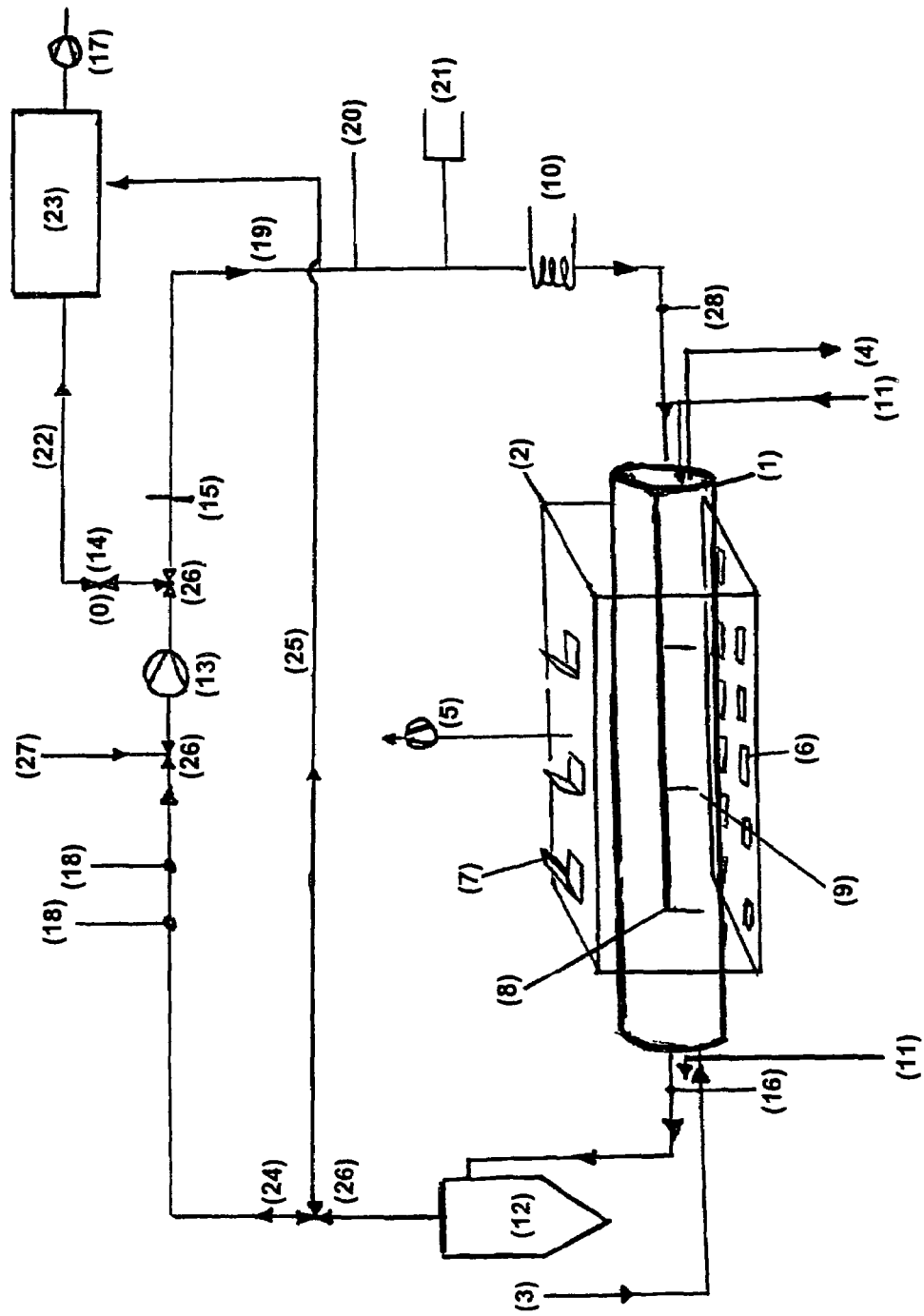
FIG. 1 shows a rotary tube furnace.

It is an object of the present invention to provide an improved process for the preparation of relevant multielement oxide active materials, which gives multielement oxide active materials which, when used as active materials in catalysts for the heterogeneously catalyzed partial oxidation of acrolein to acrylic acid, have high activity and high selectivity of the acrylic acid formation.

We have found that this object is achieved by a process for the preparation of catalytically active multielement oxide materials which contain at least one of the elements Nb and W and the elements Mo, V and Cu, the molar fraction of the element Mo, based on the total amount of all elements other than oxygen in the catalytically active multielement oxide material, being from 20 (preferably 30 or 40) to 80 mol %, the molar ratio of Mo contained in the catalytically active multi-element oxide material to V, Mo/V contained in the catalytically active multielement oxide material being from 15:1 to 1:1, the corresponding molar ratio Mo/Cu being from 30:1 to 1:3 and the corresponding molar ratio Mo/(total amount of W and Nb) being from 80:1 to 1:4, in which an intimate dry blend also containing ammonium ions is prepared from starting compounds which contain the elemental constituents of the multielement oxide material, other than oxygen, as components and said dry blend is thermally treated at elevated temperatures in an (gas) atmosphere having a low content of molecular oxygen, at least a portion of the ammonium ions contained in the intimate dry blend being decomposed at $\geq 160°$ C. with liberation of ammonia, wherein the thermal treatment is carried out as follows:

the intimate dry blend is heated at a heating rate of $\leq 10°$ C./min to a decomposition temperature in the decomposition temperature range from 240° C. to 360° C. and is kept in this temperature range until at least 90 mol % of the total amount $M^A$ of ammonia liberated altogether in the entire course of the thermal treatment of the intimate dry blend from the intimate dry blend at above 160° C. have been liberated;

the content of molecular oxygen in the (gas) atmosphere A in which the thermal treatment of the intimate dry blend takes place is reduced to $\leq 0.5\%$ by volume no later than when the intimate dry blend has reached 230° C., and this low oxygen content is maintained until at least 20, preferably at least 30, particularly preferably at least 40, mol % of the total amount $M^A$ of ammonia liberated altogether in the entire course of the thermal treatment have been liberated;

the intimate blend is taken at a rate of $\leq 10°$ C./min out of the decomposition temperature range and into the calcination temperature range of from 380 to 450° C. no earlier than when $\geq 70$ mol % (frequently when $\geq 75$ mol % or when $\geq 80$ mol % or $\geq 85$ mol % or $\geq 90$ mol %) of the total amount of $M^A$ of ammonia liberated altogether in the entire course of the thermal treatment have been liberated and the content of molecular oxygen in the atmosphere A is increased to >0.5 to 4% by volume no later than when 98 mol % or 95 mol % of the total amount $M^A$ of ammonia liberated altogether in the entire course of the thermal treatment have been liberated and the intimate dry blend is calcined at this increased oxygen content of the atmosphere A in the calcination temperature range.

Of course, in the novel process, the elements Mo, V, Cu and Nb and/or W (like all other elements other than oxygen which, if desired, are present) are contained in oxidic (and not in metallic, elemental) form in the catalytically active multi-element oxide material obtainable according to the invention.

The content of ammonium ions in the intimate dry blend to be thermally treated according to the invention is advantageously at least 5 or at least 10, preferably at least 20, particularly preferably at least 30, very particularly preferably at least 40, mol %, based on the total molar content of elemental constituents of the subsequent catalytically active multielement oxide material, other than oxygen, in the intimate dry blend. As a rule, the ammonium content, on the above basis, of the intimate dry blend, is $\leq 150$ mol % or $\leq 100$ mol %, in general $\leq 90$ mol % or $\leq 80$ mol %, frequently $\leq 70$ mol % or $\leq 60$ mol %.

In the novel process, the temperature rate at which the intimate dry blend is heated to the decomposition temperature is advantageously $\leq 8$, preferably $\leq 5$, particularly preferably $\leq 3$, very particularly preferably $\leq 2$ or $\leq 1°$ C./min. As a rule, however, this temperature rate is $\geq 0.1$, in general $\geq 0.2$, ° C./min, frequently $\geq 0.3$ or $\geq 0.4°$ C./min.

The abovementioned also applies to the temperature rate at which the intimate dry blend is brought out of the decomposition range and into the calcination range of from 380 to 480° C.

According to the invention, the decomposition temperature range is preferably from 280 to 360° C., particularly preferably from 300 to 350° C. or from 310 to 340° C.

In the novel process, the intimate dry blend is furthermore advantageously kept in the decomposition temperature range until at least 95, preferably at least 97, more preferably at least 99, mol % or all of the total amount $M^A$ of ammonia liberated altogether in the entire course of the thermal treatment of the intimate dry blend have or has been liberated.

In the novel process, the intimate dry blend is usually heated from room temperature (e.g. 20 or 25 or 30 or 35 or 40° C.) to the decomposition temperature.

In the novel process, the content of molecular oxygen in the (gas) atmosphere A in which the thermal treatment of the intimate dry blend takes place must be reduced to $\leq 0.5\%$ by volume no later than when the intimate dry blend has reached 230° C.

It is preferable according to the invention if the content of molecular oxygen is reduced to $\leq 0.3$, particularly preferably to $\leq 0.1$, % by volume. Particularly preferably, the content of molecular oxygen in the atmosphere A is insignificant in this phase of the novel process. As a rule, however, this oxygen content is $\geq 0.05\%$ by volume.

In the novel process, the content of the atmosphere A is preferably $\leq 0.5$ or $\leq 0.3$ or $\leq 0.1$ or 0% by volume even below 230° C. (e.g. even at temperatures $\geq 200°$ C.). As a rule, however, this oxygen content is $\geq 0.05\%$ by volume even below 230° C. (e.g. even at temperatures <200° C.).

Below 230° C. or 200° C., however, the gas atmosphere A in which the thermal treatment takes place may also have substantially higher oxygen contents. Below 230° C. or 200° C. in the novel process, this content of molecular oxygen can in principle be $\geq 5$ or $\geq 10$ or $\geq 15$ or $\geq 20$ or $\geq 25$ or 30% by volume or more. The thermal treatment atmosphere comprising substantially exclusively air or molecular oxygen is also possible in this temperature range.

According to the invention, the content of $\leq 0.5\%$ by volume of molecular oxygen in the atmosphere A is maintained at least until at least 20 or 30 or 40 mol %, preferably at least 50 mol %, particularly preferably at least 60 mol % or at least 70 mol % or at least 80 mol %, of the total amount $M^A$ of ammonia liberated altogether in the entire course of the thermal treatment have been liberated.

Experience has shown that it is advantageous if the content of molecular oxygen in the atmosphere A is, however, increased to >0.5 to 4% by volume even before 95 mol % of the total amount $M^A$ of ammonia liberated altogether in the entire course of the thermal treatment have been liberated. This increase in the oxygen content is preferably effected even before 90, preferably before 0.85, mol % and particularly preferably no later than when 80 mol % of the total amount $M^A$ of ammonia liberated altogether in the entire course of the thermal treatment have been liberated.

This means that it is expedient according to the invention if the range of the novel process in which the content of molecular oxygen in the atmosphere A is ≦0.5% by volume extends until 20 or 30 or 40 or 80 mol %, preferably from 50 to 70 mol %, of the total amount $M^A$ of ammonia liberated altogether in the entire course of the thermal treatment have been liberated.

If the content of molecular oxygen in the atmosphere A is increased to ≦0.5 to 4% by volume no later than when 98 mol % or 95 mol % of the total amount $M^A$ of ammonia liberated altogether in the entire course of the thermal treatment have been liberated, this increase is preferably effected to a value of ≧0.55 to 4, particularly preferably ≧0.6 to 4, % by volume. Very particularly preferably the increase in the oxygen content is effected to a value of from 1 to 3 or from 1 to 2% by volume. These values relating to increases also apply to increases in the case of all other liberated portions of the total amounts of ammonia liberated altogether, which portions are mentioned as being possible.

In the novel process, the calcination temperature range advantageously covers a temperature of the intimate dry blend of from 380 to 430° C., particularly preferably from 390 to 420° C.

In the novel process, the decomposition temperature range is that temperature range after which the decomposition of the ammonium ions contained in the intimate dry blend to be thermally treated according to the invention is substantially complete.

In the novel process, the formation of the catalytically active multielement oxide takes place in the calcination temperature range.

As a rule, the calcination in the calcination temperature range will last for at least 10, preferably at least 20, particularly preferably at least 30, minutes. As a rule, the calcination in the calcination temperature range continues for ≦2 hours, frequently ≦1.5 hours or ≦1 hour.

After calcination is complete, the calined material is usually cooled. As a rule, it is cooled to room temperature (e.g. to 20° C. or to 25° C. or to 30° C. or to 35° C. or to 40° C.).

It is expedient according to the invention if the calcined material is cooled to ≦100° C. within a period of ≦5, preferably ≦4, particularly preferably ≦3 or ≦2, hours. As a rule, however, this cooling period is not less than 0.5 hour.

Advantageously, the cooling of the calcined material is effected in a (gas) atmosphere A which surrounds it and whose content of molecular oxygen is ≦5 or ≦4 or ≦3 or ≦2 or ≦1 or ≦0.5% by volume, preferably ≦0.3 or ≦0.1 or 0% by volume, as a rule ≧0.05% by volume. This oxygen content is expediently established at the start of bringing the calcined material, still present in the calcination temperature range, out of the calcination temperature range by reducing the temperature.

Once the calcined material has cooled to ≦350° C. or ≦300° C. or ≦250° C., the further cooling can also be effected in a (gas) atmosphere A whose content of molecular oxygen is ≧5 or ≧10 or ≧15 or ≧20 or ≧25 or ≧30% by volume or more.

A (gas) atmosphere A comprising substantially exclusively air or molecular oxygen is also possible during the further cooling below this temperature.

In addition to the described contents of molecular oxygen, the atmosphere A in which the thermal treatment of the intimate dry blend takes place is substantially composed of the components escaping in gaseous form from the intimate dry blend and of inert gas. The term inert gases is understood as meaning all those gases which do not chemically react with the dry material to be thermally treated according to the invention. Examples of inert gases are $N_2$ or noble gases. The atmosphere A will contain steam in particular when the intimate dry blend contains water of hydration. As a rule, the steam content of the atmosphere A does not exceed 20% by volume at any time during the novel thermal treatment. As a rule, it is even ≦10% by volume at all times.

In the novel process, the ammonia content of the (gas) atmosphere A usually passes through a maximum which is usually ≦10, frequently ≦8, % by volume and generally ≦7% by volume. Usually, however, it is above 1, frequently above 2 or 3, % by volume.

The ammonia content of the atmosphere A usually passes through its maximum before the intimate dry blend has reached the calcination temperature range.

This means that, in the calcination temperature range, the maximum ammonia content of the atmosphere A is as a rule ≦2 or ≦1% by volume. However, it is usually >0% by volume.

(Arithmetically) averaged over the total time during which the intimate dry blend is in the calcination temperature range, the $NH_3$ content of the atmosphere A is as a rule ≦1, preferably ≦0.5, % by volume. (Arithmetically) averaged over the total time during which the intimate dry blend is in the temperature range >160° C. and ≦360° C., the $NH_3$ content of the atmosphere A is usually 1 or 1.5 or from 2 to 8% by volume, in general from 1 to 4% by volume.

In the novel process, usually no external ammonia is added to the (gas) atmosphere A, i.e. the only ammonia source usually comprises the ammonium ions incorporated into the intimate dry blend. However, it may be expedient in the novel process to remove (gas) atmosphere A continuously and to recycle it to a certain extent (i.e. to recycle it to the intimate dry blend to be thermally treated).

According to the invention, it is advantageous to stop the calcination before $MoO_3$ is detectable in the X-ray diffraction pattern. However, $MoO_3$ contents of up to 30 or up to 20% by weight are tolerable in the multielement oxide active materials obtainable according to the invention.

In addition to the elements Nb and/or W, and Mo, V and Cu, the multielement oxide active materials obtainable according to the invention may additionally contain, for example, the elements Ta, Cr, Ce, Ni, Co, Fe, Mn, Zn, Sb, Bi, alkali metal (Li, Na, K, Rb, Cs), H, alkaline earth metal (Mg, Ca, Sr, Ba), Si, Al, Ti and Zr. According to the invention, however, the multielement oxide active material can of course also consist only of the elements Nb and/or W and Mo, V and Cu.

Catalytically active multielement oxide materials obtainable according to the invention and particularly suitable as active material for catalysts for the heterogeneously catalyzed partial gas-phase oxidation of acrolein to acrylic acid (and of methacrolein to methacrylic acid and of propane to acrylic acid; the novel products of the process are also suitable for these heterogeneously catalyzed gas-phase partial oxidations) satisfy the following stoichiometry I $$Mo_{12}V_aX^1_bX^2_cX^3_dX^4_eX^5_fX^6_gO_n \qquad (I)$$

where:
$X^1$ is W, Nb, Ta, Cr and/or Ce,
$X^2$ is Cu, Ni, Co, Fe, Mn and/or Zn, $X^3$ is Sb and/or Bi,
$X^4$ is one or more alkali metals (Li, Na, K, Rb, Cs) and/or H,
$X^5$ is one or more alkaline earth metals (Mg, Ca, Sr, Ba),
$X^6$ is Si, Al, Ti and/or Zr,
a is from 1 to 6,
b is from 0.2 to 4,
c is from 0.5 to 18,
d is from 0 to 40,
e is from 0 to 2,
f is from 0 to 4,
g is from 0 to 40 and
n is a number which is determined by the valency and frequency of the elements other than oxygen in I, and in which the variables are to be chosen within the specified ranges with the proviso that the molar fraction of the element Mo, based on the total amount of all elements other than oxygen in the multielement oxide material (I), is from 20 to 80 mol %, the molar ratio of Mo contained in the catalytically active multielement oxide material (I) to V, Mo/V, contained in the catalytically active multielement oxide material (I) is from 15:1 to 1:1, the corresponding molar ratio Mo/Cu is from 30:1 to 1:3 and the corresponding molar ratio Mo/(total amount of W and Nb) is from 80:1 to 1:4.

Preferred among the active multielement oxide materials (I) are those in which the variables are in the following ranges:
$X^1$ is W, Nb and/or Cr,
$X^2$ is Cu, Ni, Co and/or Fe,
$X^3$ is Sb,
$X^4$ is Na and/or K,
$X^5$ is Ca, Sr and/or Ba,
$X^6$ is Si, Al and/or Ti,
a is from 2.5 to 5,
b is from 0.5 to 2,
c is from 0.5 to 3,
d is from 0 to 2,
e is from 0 to 0.2,
f is from 0 to 1,
g is from 0 to 15 and
n is a number which is determined by the valency and frequency of the elements other than oxygen in I.

Very particularly preferably, however, the following multielement oxide active materials II are direct products of the novel process:

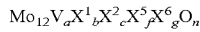 (II), where:
$X^1$ is W and/or Nb,
$X^2$ is Cu and/or Ni,
$X^5$ is Co and/or Sr,
$X^6$ Si and/or Al,
a is from 3 to 4.5,
b is from 1 to 1.5,
c is from 0.75 to 2.5,
f is from 0 to 0.5,
g is from 0 to 8 and
n is a number which is determined by the valency and frequency of the elements other than oxygen in II, and in which the variables are to be chosen within the specified ranges with the proviso that the molar fraction of the element Mo, based on the total amount of all elements other than oxygen in the multielement oxide active material (II), is from 20 to 80 mol %, the molar ratio of Mo contained in the catalytically active multielement oxide material (II) to V, Mo/V, contained in the catalytically active multielement oxide material (II) is from 15:1 to 1:1, the corresponding molar ratio Mo/Cu is from 30:1 to 1:3 and the corresponding molar ratio Mo/(total amount of W and Nb) is from 80:1 to 1:4.

In the novel process, sources (starting compounds) of the elemental constituents of the desired multielement oxide active material, other than oxygen, in the respective stoichiometric ratio desired in the multielement oxide active material, are used as starting materials for the preparation of such novel direct products of the process, said sources being suitable in a manner known per se, and a very intimate, preferably finely divided, dry blend is produced from said sources and is then subjected to the novel thermal treatment, it being possible to carry out the thermal treatment before or after the shaping to catalyst moldings of a certain geometry. According to the invention, said treatment is advantageously carried out beforehand. The sources can be either oxides or those compounds which can be converted into oxides by heating, at least in the presence of oxygen. In addition to the oxides, particularly suitable starting compounds are therefore halides, nitrates, formates, oxalates, acetates, carbonates and hydroxides.

Suitable starting compounds of Mo, V, W and Nb are also oxo compounds thereof (molybdates, vanadates, tungstates and niobates) or the acids derived from these. Oxygen-containing sources are advantageous for the novel process.

The content of ammonium ions which is required according to the invention in the intimate dry blend can be realized in a simple manner by incorporating a corresponding amount of ammonium ions into the intimate dry blend. The ammonium ions can be expediently introduced into the intimate dry blend, for example, by using, as sources of the elements Mo, V, W or Nb, the corresponding ammonium oxometallates. Examples of these are ammonium metaniobate, ammonium metavanadate, ammonium heptamolybdate tetrahydrate and ammonium paratungstate heptahydrate. However, ammonium donors, such as $NH_4NO_3$ or $NH_4Cl$ or ammonium acetate or ammonium carbonate or ammonium bicarbonate or $NH_4OH$ or $NH_4CHO_2$ or ammonium oxalate, can of course also be incorporated into the intimate dry blend to be thermally treated, independently of the starting compounds required as sources of the multielement oxide active material constituents.

The thorough mixing of the starting compounds can be carried out in principle in dry or wet form. If it is effected in dry form, the starting compounds are expediently used in the form of finely divided powder and, after the mixing, compressed (e.g. tableted) to give catalyst moldings of the desired geometry, which are then subjected to the novel thermal treatment.

However, the thorough mixing is preferably effected in wet form. Usually, the starting compounds are mixed with one another in the form of an aqueous solution and/or suspension. Particularly intimate dry blends are obtained in the mixing method described when exclusively sources and starting compounds present in dissolved form are employed. A preferably used solvent is water. Thereafter, the aqueous material (solution or suspension) is dried and the intimate dry blend thus obtained is, if required, subjected directly to the thermal treatment according to the invention. The drying process is preferably effected by (the outlet temperatures are as a rule from 100 to 150° C.) and immediately after the preparation of the aqueous solution or suspension. The resulting powder can be directly molded by compression. Frequently, however, it proves to be too finely divided for direct further processing and is then therefore expediently kneaded with addition of, for example, water.

The addition of a lower organic carboxylic acid (e.g. acetic acid) often proves advantageous during kneading (typical added amounts are from 5 to 10% by weight, based on powder material used).

The resulting kneaded material is then either shaped to give the desired catalyst geometry, dried and then subjected to the novel thermal treatment (leads to unsupported catalysts) or is calcined in the unmolded form and then milled to give a powder (usually <80 µm, preferably <50 µm, particularly preferably <30 µm, as a rule ≧1 µm), which is usually applied as moist material to inert supports with addition of a small amount of water and, if required, further conventional binders. After the end of the coating, drying is carried out again and a ready-to-use coated catalyst is thus obtained. If the thorough mixing of the starting compounds is effected in the form of, for example, an aqueous solution, inert porous supports may also be impregnated with said solution, dried and then subjected to the thermal treatment according to the invention to give supported catalysts. In the preparation of coated catalysts, the coating of the supports can also be carried out before the novel thermal treatment, for example with the moistened spray-dried powder.

Support materials suitable for coated catalysts are, for example, porous or nonporous aluminas, silica, thorium dioxide, zirconium dioxide, silicon carbide or silicates, such as magnesium silicate or aluminum silicate (e.g. steatite of the type C 220 from CeramTec).

The supports may have a regular or irregular shape, those having a regular shape and pronounced surface roughness, e.g. spheres or hollow cylinders coated with chips, being preferred.

The use of substantially nonporous, spherical steatite supports which have a rough surface (e.g. steatite of the type C 220 from CeramTec) and whose diameter is from 1 to 8 mm, preferably from 4 to 5 mm, is preferred. However, the use of cylinders as supports whose length is from 2 to 10 mm and whose external diameter is from 4 to 10 mm is also suitable. In the case of annular supports, the wall thickness is moreover usually from 1 to 4 mm. Annular supports preferably to be used have a length of from 2 to 6 mm, an external diameter of from 4 to 8 mm and a wall thickness of from 1 to 2 mm. Rings measuring 7 mm×3 mm×4 mm (external diameter×length×internal diameter) are also particularly suitable as supports.

The coating of the supports with finely divided multielement oxide active material obtainable according to the invention or with the finely divided precursor material thereof (intimate dry blend) to be subjected to the thermal treatment according to the invention is carried out as a rule in a rotatable container, as disclosed, for example, in DE-A 2909671, EP-A 293859 or EP-A 714700. The procedure of EP-A 714700 is preferred.

The support is expediently moistened for coating the supports with the powder material to be applied. After the application, drying is usually effected by means of hot air. The coat thickness of the powder material applied to the support is expediently chosen to be in the range of from 10 to 1 000 µm, preferably from 50 to 500 µm, particularly preferably from 150 to 250 µm.

In the case of unsupported catalysts, the shaping can, as stated above, also be effected before or after the novel thermal treatment is carried out.

For example, unsupported catalysts can be prepared from the powder form of the multielement oxide active material obtainable according to the invention or its precursor material not as yet subjected to the thermal treatment (the intimate dry blend), by compaction to give the desired catalyst geometry (e.g. by tableting or extrusion), it being possible, if required, to add assistants, e.g. graphite or stearic acid as lubricants and/or molding assistants and/or reinforcing agents, such as microfibers of glass, asbestos, silicon carbide or potassium titanate. Suitable geometries for unsupported catalysts are, for example, solid cylinders or hollow cylinders having an external diameter and a length of from 2 to 10 mm. In the case of the hollow cylinders, a wall thickness of from 1 to 3 mm is expedient. The unsupported catalyst can of course also have a spherical geometry, it being possible for the sphere diameter to be from 2 to 10 mm.

The multielement oxide active materials obtainable according to the invention can of course also be used in powder form, i.e. without shaping to give certain catalyst geometries, as catalysts for the heterogeneously catalyzed partial oxidation of acrolein to acrylic acid or methacrolein to methacrylic acid or propane to acrylic acid (for example also in a fluidized bed).

However, the novel process is also suitable for the preparation of multielement oxide active materials of the formula III $$[A]_p[B]_q[C]_r \qquad (III),$$

where:

A is $Mo_{12}V_aX^1{}_bX^2{}_cX^3{}_dX^4{}_eX^5{}_fX^6{}_gO_x$,

B is $X^7_1Cu_hH_iO_y$,

C is $X^8_1Sb_jH_kO_z$, $X^1$ is W, Nb, Ta, Cr and/or Ce, preferably W, Nb and/or Cr, $X^2$ is Cu, Ni, Co, Fe, Mn and/or Zn, preferably Cu, Ni, Co and/or Fe, $X^3$ is Sb and/or Bi, preferably Sb, $X^4$ is Li, Na, K, Rb, Cs and/or H, preferably Na and/or K, $X^5$ is Mg, Ca, Sr and/or Ba, preferably Ca, Sr and/or Ba, $X^6$ is Si, Al, Ti and/or Zr, preferably Si, Al and/or Ti, $X^7$ is Mo, W, V, Nb and/or Ta, preferably Mo and/or W, $X^8$ is Cu, Ni, Zn, Co, Fe, Cd, Mn, Mg, Ca, Sr and/or Ba, preferably Cu and/or Zn, particularly preferably Cu, a is from 1 to 8, preferably from 2 to 6, b is from 0.2 to 5, preferably 0.5 to 2.5, c is from 0 to 23, preferably from 0 to 4, d is from 0 to 50, preferably from 0 to 3, e is from 0 to 2, preferably from 0 to 0.3, f is from 0 to 5, preferably from 0 to 2, g is from 0 to 50, preferably from 0 to 20, h is from 0.3 to 2.5, preferably from 0.5 to 2, particularly preferably from 0.75 to 1.5, i is from 0 to 2, preferably from 0 to 1, j is from 0.1 to 50, preferably from 0.2 to 20, particularly preferably from 0.2 to 5, k is from 0 to 50, preferably from 0 to 20, particularly preferably from 0 to 12, x, y and z are numbers which are determined by the valency and frequency of the elements other than oxygen in A, B and C, p and q are positive numbers, r is 0 or a positive number, preferably a positive number, the ratio p/(q+r) being from 20:1 to 1:20, preferably from 5:1 to 1:14, particularly preferably from 2:1 to 1:8, and, where r is a positive number, the ratio q/r being from 20:1 to 1:20, preferably from 4:1 to 1:4, particularly preferably from 2:1 to 1:2, very particularly preferably 1:1, which contain the moiety $[A]_p$ in the form of three-dimensional regions (phases) A having the chemical composition A: $Mo_{12}VaX^1_bX^2_cX^3_dX^4_eX^5_fX^6_gO_x$, the moiety $[B]_q$ in the form of three-dimensional regions (phases) B having the chemical composition B: $X_1^7Cu_hH_iO_y$, and the moiety $[C]_r$ in the form of three-dimensional regions (phases) C having the chemical composition C: $X_1^8Sb_jH_kO_z$, the regions A, B and, if required, C being distributed relative to one another as in a mixture of finely divided A, finely divided B and, if required, finely divided C, and in which all variables are to be chosen within the specified ranges with the proviso that the molar fraction of the element Mo, based on the total amount of all elements other than oxygen in the multielement oxide active material (III), is from 20 to 80 mol %, the molar ratio of the Mo contained in the catalytically active multielement oxide material (III) to V, Mo/V, contained in the catalytically active multielement oxide material (III) is from 15:1 to 1:1, the corresponding molar ratio of Mo/Cu is from 30:1 to 1:3 and the corresponding molar ratio Mo/(total amount of W and Nb) is from 80:1 to 1:4.

Preferred multielement oxide active materials II are those whose ranges A have a composition in the following stoichiometric range of the formula IV $$Mo_{12}V_aX^1_bX^2_cX^5_fX^6_gO_x \qquad (IV),$$

where
$X^1$ is W and/or Nb,
$X^2$ is Cu and/or Ni,
$X^5$ is Ca and/or Sr,
$X^6$ is Si and/or Al,
a is from 2 to 6,
b is from 1 to 2,
c is from 1 to 3,
f is from 0 to 0.75,
g is from 0 to 10 and
x is a number which is determined by the valency and frequency of the elements other than oxygen in (IV).

The term phase used in connection with the multielement oxide active materials III means three-dimensional regions whose chemical composition differs from that of their environment. The phases are not necessarily X-ray homogeneous. As a rule, the phase A is a continuous phase in which particles of the phase B and, if required, C are dispersed.

The finely divided phases B and, if required, C advantageously consist of particles whose diameter, i.e. the longest distance passing through the center of gravity of the particle and connecting two points present on the surface of the particle, is up to 300 µm, preferably from 0.1 to 200 µm, particularly preferably from 0.5 to 50 µm, very particularly preferably from 1 to 30 µm. However, particles having a diameter of from 10 to 80 µm or from 75 to 125 µm are also suitable.

In principle, the phases A, B and, if required, C in the multimetal oxide active materials III obtainable according to the invention may be present in amorphous and/or crystalline form.

It is advantageous if the phase B consists of crystallites of oxometallates or contains such oxometallate crystallites (=oxide crystallites) which have the X-ray diffraction pattern, and hence the crystal structure type, of at least one of the following copper molybdates. The source of the associated X-ray diffraction fingerprint is shown in brackets.

$Cu_4Mo_6O_{20}$ [A. Moini et al., Inorg. Chem. 25 (21) (1986) 3782-3785],
$Cu_4Mo_5O_{17}$ [Index card 39-181 of the JCPDS-ICDD Index (1991)],
α-$CuMoO_4$ [Index card 22-242 of the JCPDS-ICDD Index (1991)],
$Cu_6Mo_5O_{18}$ [Index card 40-865 of the JCPDS-ICDD Index (1991)],
$Cu_{4-x}Mo_3O_{12}$ where X is from 0 to 0.25 [Index card 24-56 and 26-547 of the JCPDS-ICDD Index (1991)],
$Cu_6Mo_4O_{15}$ [Index card 35-17 of the JCPDS-ICDD Index (1991)],
$Cu_3(MoO_4)_2(OH)_2$ [Index card 36-405 of the JCPDS-ICDD Index (1991)],
$Cu_3Mo_2O_9$ [Index card 24-55 and 34-637 of the JCPDS-ICDD Index (1991)],
$Cu_2MoO_5$ [Index card 22-607 of the JCPDS-ICDD Index (1991)].

The phase B preferably contains oxometallates which have the X-ray diffraction pattern, and hence the crystal structure type, of the following copper molybdate:

$CuMoO_4$-III having the wolframite structure according to Russian Journal of Inorganic Chemistry 36 (7) (1991), 927-928, table 1.

Preferred among these are those having the following stoichiometry V $$Cu_1Mo_AW_BV_CNb_DTa_EO_y \cdot (H_2O)_F \qquad (V),$$

where
1/(A+B+C+D+E) is from 0.7 to 1.3, preferably from 0.85 to 1.15, particularly preferably from 0.95 to 1.05, very particularly preferably 1,
F is from 0 to 1,
B+C+D+E is from 0 to 1, preferably from 0 to 0.7, and
Y is a number which is determined by the valency and frequency of the elements other than oxygen.

Particularly preferred among these are those having the stoichiometry VI, VII or VIII:

$$Cu_1Mo_AW_BV_CO_y \qquad (VI),$$

where
1/(A+B+C) is from 0.7 to 1.3, preferably from 0.85 to 1.15, particularly preferably from 0.95 to 1.05, very particularly preferably 1,
B+C is from 0 to 1, preferably from 0 to 0.7, and
y is a number which is determined by the valency and frequency of the elements other than oxygen;

$$Cu_1Mo_AW_BO_y \qquad (VI),$$

where
1/(A+B) is from 0.7 to 1.3, preferably from 0.85 to 1.15, particularly preferably form 0.95 to 1.05, very particularly preferably 1,
A and B is from 0 to 1 and
y is a number which is determined by the valency and frequency of the elements other than oxygen;

$$Cu_1Mo_AW_BO_y \qquad (VII),$$

where
1/(A+C): is from 0.7 to 1.3, preferably from 0.85 to 1.15, particularly preferably from 0.95 to 1.05, very particularly preferably 1, A and C is from 0 to 1 and y is a number which is determined by the valency and frequency of the elements other than oxygen.

The preparation of such oxometallates is disclosed, for example, in EP-A 668 104.

Suitable phases B are also those which contain the oxometallates of the following stoichiometry IX $$Cu_1Mo_AW_BV_CNb_DTa_EO_y \quad (IX),$$

where

1/(A+B+C+D+E) is from 0.7 to 1.3, preferably from 0.85 to 1.15, particularly preferably from 0.95 to 1.05, very particularly preferably 1, (B+C+D+E)/A is from 0 to 1, preferably from 0.05 to 0.3, particularly preferably from 0.075 to 0.15, very particularly preferably 0.11, and y is a number which is determined by the valency and frequency of the elements other than oxygen, and of the structure type defined as the HT copper molybdate structure, which is characterized by an X-ray diffraction pattern (fingerprint) whose most characteristic and most intense diffraction lines, stated as interplanar spacings d [Å], are as follows:

6.79±0.3
3.56±0.3
3.54±0.3
3.40±0.3
3.04±0.3
2.96±0.3
2.67±0.2
2.66±0.2
2.56±0.2
2.36±0.2
2.35±0.2
2.27±0.2
2.00±0.2
1.87±0.2
1.70±0.2
1.64±0.2
1.59±0.2
1.57±0.2
1.57±0.2
1.55±0.2
1.51±0.2
1.44±0.2.

Where the phase B contains a mixture of different oxometallates, a mixture of oxometallates having the wolframite structure and HT copper molybdate structure is preferred. The weight ratio of crystallites having the HT copper molybdate structure to crystallites having the wolframite structure may be from 0.01 to 100, from 0.1 to 10, from 0.25 to 4 and from 0.5 to 2.

The preparation of oxometallates IX is disclosed, for example, in DE-A 195 28 646.

The C phase preferably consists of crystallites which have the trirutile structure type of α- and/or β-copper antimonate $CuSb_2O_6$. α-$CuSb_2O_6$ crystallizes in a tetragonal trirutile structure (E.-O. Giere et al., J. Solid State Chem. 131 (1997), 263-274), whereas β-$CuSb_2O_6$ has a monoclinically distorted trirutile structure (A. Nakua et al., J. Solid State Chem. 91 (1991), 105-112, or comparative diffraction pattern in Index card 17-284 in the JCPDS-ICDD Index 1989). Moreover, preferred C phases are those which have the pyrochlore structure of the mineral parzite, a copper antimony oxide hydroxide having the variable composition $Cu_ySb_{2-x}(O, OH, H_2O)_{6-7}(y≦2.0≦x≦1)$ (B. Mason et al., Mineral. Mag. 30 (1953), 100-112, or comparative diagram in Index card 7-303 of the JCPDS-ICDD Index 1996).

Furthermore, the C phase may consist of crystallites which have the structure of the copper antimonate $Cu_9Sb_4O_{19}$ (S. Shimada et al., Chem. Lett. (1983), 1875-1876 or S. Shimada et. al., Thermochim. Acta 133 (1988), 73-77, or comparative diagram in Index card 45-54 of the JCPDS-ICDD Index) and/or the structure of $Cu_4SbO_{4.5}$ (S. Shimada et al., Thermochim. Acta 56 (1982), 73-82 or S. Shimada et al., Thermochim. Acta 133 (1988), 73-77, or comparative diagram in Index card 36-1106 of the JCPDS-ICDD Index).

Of course, the regions C may also consist of crystallites which are a mixture of the abovementioned structures.

The intimate dry blends on which the multielement oxide active materials of the formula III are based and which are to be subjected to the thermal treatment according to the invention can be obtained, for example, as described in WO 02/24327, DE-A 4405514, DE-A 4440891, DE-A 19528646, DE-A 19740493, EP-A 756894, DE-A 19815280, DE-A 19815278, EP-A 774297, DE-A 19815281, EP-A 668104 and DE-A 19736105. According to the invention, it is merely necessary to take into account the concomitant incorporation of ammonium ions.

This means that all intimate dry blends produced in the exemplary embodiments in the abovementioned publications can be subjected to the thermal treatment according to the invention and lead to direct products of the process which are very useful for catalysts for the heterogeneously catalyzed partial gas-phase oxidation of acrolein to acrylic acid.

The fundamental principle of the preparation of intimate dry blends which, in the novel treatment, lead to advantageous multielement oxide active materials of the formula III comprises preforming at least one multielement oxide material B ($X_1^7Cu_hH_iO_y$) as starting material 1 and, if required, one or more multielement oxide materials C($X_1^8Sb_jH_kO_z$) as starting material 2 either separately from one another or together with one another in finely divided form and then bringing the starting materials 1 and, if required, 2 into intimate contact with a mixture which contains sources of the elemental constituents of the multielement oxide material A $$Mo_{12}V_aX_a X_b^1 X_c^2 X_d^3 X_e^4 X_f^5 X_g^6 O_x \quad (A),$$

in a composition corresponding to the stoichiometry A, in the desired ratio (according to the formula III), and, if required, drying the resulting intimate mixture. According to the invention, all that is important is that either the sources of the elemental constituents of the multielement oxide material A contain ammonium ions and/or completely decomposable salts containing ammonium ions, such as $NH_4NO_3$, $NH_4Cl$, ammonium acetate, etc., are added when bringing into intimate contact.

The components of the starting materials 1 and, if required, 2 can be brought into contact with the mixture (starting material 3) containing the sources of the elemental constituents of the multimetal oxide material A either in dry form or in wet form. In the latter case, it is merely necessary to ensure that the preformed phases (crystallites) B and, if required, C do not go into solution. In the aqueous medium, the latter is usually ensured at a pH which does not deviate too greatly from 7 and at temperatures which are not too high. If the bringing into intimate contact is effected in wet form, the intimate dry blend to be subjected to the thermal treatment according to the invention is usually finely dried (for example by spray drying). In the course of dry mixing, such a dry material is automatically obtained. The phases B and, if required, C preformed in finely divided form can of course also be incorporated into a plastically deformable mixture which contains the sources of the elemental constituents of the multimetal oxide material A, as recommended in DE-A 10046928. Of course, the components of the starting materials 1 and, if required, 2 can be brought into intimate contact with the sources of the multielement oxide material A (starting material 3) also as described in DE-A 19815281.

According to the invention, it may also be expedient to adopt a procedure in which the sources of the multielement oxide material A are thoroughly mixed (for example, dissolved and/or suspended in an aqueous medium and the aqueous mixture then spray dried) and the resulting finely divided starting material 3 is mixed with the finely divided starting material 1 and, if required 2, and kneaded with one another with addition of water and, if required, other plasticizers. The mixing can be effected in a special mixing apparatus outside the kneader or in the kneader itself (change of running direction). The latter is advantageous. The kneaded material is then extruded and the extrudates are dried. The extrudates can subsequently be subjected, as described, to the thermal treatment according to the invention. The resulting calcination material is then usually milled and is used as described in EP-A 714700 for the preparation of coated catalyst.

Suitable sources of the multielement oxide material A are in principle all those which are also suitable as sources for the multielement oxide materials I.

Suitable plasticizers are substantially all solvents which vaporize substantially without residue at up to about 360° C. or decompose substantially without residue.

The plasticizer is expediently chosen so that it thoroughly wets the finely divided dry blend of the starting materials 1, 3 and, if required, 2. Suitable plasticizers in addition to water are carboxylic acids, which may be branched or straight-chain, saturated or unsaturated, e.g. formic acid and acetic acid, primary or secondary $C_1$- to $C_8$-alcohols, such as methanol, ethanol or 2-propanol, and also aldehydes or ketones, such as acetone, and mixtures thereof.

Kneaders which may be used are, for example, continuous screw kneaders or trough kneaders. Continuous screw kneaders have one or more screws which are parallel to the axis and arranged in a cylindrical housing and have on a shaft kneading and transport elements which convey the material added at one end of the kneader to the outlet end of the kneader and at the same time effect plastication and homogenization. Trough kneaders having at least two horizontally mounted rotors, for example a twin-blade trough kneader having two counterrotatable kneading blades in a double-depression trough, are expedient in terms of application technology. The rotors may have different shapes, such as a sigma, masticator or hub shape, etc. The kneaders may operate batchwise or continuously. Alternatively, it is also possible to use high-speed intensive mixers, such as plough share mixers or inclined mixers, or a comparatively low-speed Simpson mixer, which, if required, are equipped with high-speed knife elements.

It is advantageous if the kneading is effected at less than 90° C., preferably less than 80° C., particularly preferably less than 60° C. As a rule, the temperature during the kneading is more than 0° C., in general from 20 to 45° C.

It is furthermore advantageous if the kneading takes less than 10, preferably less than 3, hours, particularly preferably less than 1 hour. As a rule, the kneading takes more than 15 minutes.

The plastic (plastic or pasty denotes a consistency which is coherent and does not consist of discrete particles like powder and is deformable only under the action of a certain force and does not, like a solution or suspension, readily assume the shape of a vessel) material obtained after the kneading can be shaped directly into moldings of any desired geometry and, after they have been dried, these moldings can be subjected to the thermal treatment according to the invention, with the result that unsupported catalysts can be directly obtained. The use of a screw extruder (alternatively, an Alexander unit or a ram extruder can be used) is particularly suitable for this purpose. Frequently, the extrudate has a diameter of, for example, from 1 to 20 mm, frequently from 3 to 10 mm, over a length of, for example, from 0.5 to 20 cm. As described above, the extrudates can then be dried, thermally treated and milled and the milled material can be processed to give coated catalysts. The drying is carried out, as a rule, at from 50 to 180° C., in general at from about 120 to 130° C. (expediently in an air stream).

According to the invention, the finely divided starting materials 1, 2 generally advantageously consist of particles whose maximum diameter d (longest distance passing through the center of gravity of the particle and connecting two points present on the surface of the particles) is from >0 to 300 μm, preferably from 0.01 to 100 μm, particularly preferably from 0.05 to 20 μm. However, the particle diameter d can of course also be from 0.01 to 150 μm or from 0.5 to 50 μm.

It is possible for the starting materials 1, 2 to be used according to the invention to have a specific surface area O (determined according to DIN 66131 by gas adsorption ($N_2$) according to Brunner-Emmert-Teller, (BET)) which is $\leq 80$ m$^2$/g, frequently $\leq 50$ or $\leq 10$ and in some cases $\leq 1$ m$^2$/g. As a rule, O>0.1 m$^2$/g.

In principle, according to the invention, the starting materials 1, 2 can be used in amorphous and/or crystalline form.

It is advantageous for the starting materials 1, 2 to consist of crystallites of oxometallates B (for example those of the formulae V to IX) and crystallites of oxometallates C, as described above. As stated above, such oxometallates B are obtainable, for example, by the procedures of EP-A 668 104 or DE-A 19 528 646. However, the preparation processes of DE-A 44 05 514 and of DE-A 44 40 891 can also be used.

In principle, multielement oxide materials B containing oxometallates B or consisting of oxometallates B can be prepared in a simple manner by producing, from suitable sources of their elemental constituents, a very intimate, preferably finely divided dry blend having a composition corresponding to their stoichiometry, and calcining said dry blend at temperatures (material temperatures) of from 200 to 1000° C., preferably from 250 to 900° C. or from 700 to 850° C., for several hours under inert gas, e.g. nitrogen, or a mixture of inert gas and oxygen or preferably in the air, it being possible for the duration of calcination to be from a few minutes to a few hours. The calcination atmosphere may additionally contain steam. Calcination under pure oxygen is likewise possible. Suitable sources of the elemental constituents of the multimetal oxide material B are those compounds which are already oxides and/or those compounds which can be converted into oxides by heating, at least in the presence of oxygen. In addition to the oxides, suitable such starting compounds are in particular halides, nitrates, formates, oxalates, citrates, acetates, carbonates, ammine complex salts, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ or ammonium oxalate, which decompose and/or can be decomposed at the latest during the subsequent calcination to give compounds escaping in gaseous form, may additionally be incorporated).

The thorough mixing of the starting compounds for the preparation of multielement oxide materials B can be effected in dry form or in wet form. If it is effected in dry form, the starting compounds are expediently used in the form of finely divided powder and, 20: after mixing and, if required, compaction, are subjected to the calcination. However, the thorough mixing is preferably effected in wet form. Usually, the starting compounds are mixed with one another in the form of an aqueous solution and/or suspension. In the drying method described, particularly intimate dry blends are obtained when exclusively dissolved sources of the elemental constituents are used as starting materials. A preferably used solvent is water. The aqueous material obtained is then dried, the drying process preferably being effected by spray drying of the aqueous mixture at outlet temperatures of from 100 to 150° C. The dryed material is then calcined as described above.

A preferred method for the preparation of oxometallates B ($X^7{}_1Cu_hH_jO_y$, where X=Mo and/or W) comprises adding an aqueous ammoniacal solution of copper carbonate (for example, having the composition $Cu(OH)_2CO_3$) or copper acetate and/or copper formate to an aqueous solution of ammonium heptamolybdate and ammonium paratungstate, drying, e.g. spray drying, the resulting mixture and calcining the resulting dry blend in the manner described, if required after subsequent kneading and extrusion as well as drying.

In another variant for the preparation of the multielement oxide materials B, the thermal treatment of the mixture of the starting compounds used is effected in a pressure-resistant vessel (autoclave) in the presence of steam at superatmospheric pressure and at from >100 to 600° C. The pressure range is typically up to 500, preferably up to 250, atm. Particularly advantageously, this hydrothermal treatment is carried out in the temperature range from >100 to 374.15° C. (critical temperature of water), in which steam and liquid water coexist under the resulting pressures.

The multielement oxide materials B obtainable as described above, which may contain oxometallates B of an individual structure type or a mixture of oxometallates B of different structure types, or consist exclusively of oxometallates B of an individual structure type or of a mixture of oxometallates of different structure types, can then be used, if required after milling and/or classification to desired sizes, as starting material 1 required according to the invention.

The multimetal oxide materials C can in principle be prepared in the same way as the multimetal oxide materials III. In the case of the multimetal oxide material C, the calcination of the intimate dry blend is expediently effected at temperatures (material temperatures) of from 250 to 1200° C., preferably from 250 to 850° C. The calcination can be carried out under inert gas, e.g. nitrogen, or under a mixture of inert gas and oxygen, e.g. air, or under pure oxygen. Calcination under a reducing atmosphere is also possible. For example, hydrocarbons, such as methane, aldehydes, such as acrolein or ammonia can be used as such reducing gases. The calcination can, however, also be carried out under a mixture of $O_2$ and reducing gases, as described, for example, in DE-A 4335973. In a calcination under reducing conditions, however, it must be ensured that the metallic constituents are not reduced to the element. Here too, the required duration of calcination (as a rule a few hours) generally decreases with increasing calcination temperature.

According to the invention, preferably used multielement oxide materials C are those which are obtainable by preparing a dry blend from sources of the elemental constituents of the multielement oxide material C which contain at least a part, preferably the total amount, of the antimony in the oxidation state +5, and calcining said dry blend at temperatures (material temperatures) of from 200 to 1200° C., preferably from 200 to 850° C., particularly preferably from 300 to 600° C.

Such multimetal oxide materials C are obtainable, for example, by the preparation methods described in detail in DE-A 24 07 677. Preferred among these is the procedure in which antimony trioxide or $Sb_2O_4$ is oxidized in an aqueous medium by means of hydrogen peroxide in an amount which is below the stoichiometric amount or is equal to it or exceeds it, at from 40 to 100° C., to give antimony (V) oxide hydroxide, aqueous solutions and/or suspensions of suitable starting compounds of the other elemental constituents of the multimetal oxide material C are added before this oxidation, during this oxidation and/or after this oxidation, the resulting aqueous mixture is then dried (preferably spray-dried, entrance temperature: from 200 to 300° C., exit temperature: from 80 to 130° C., frequently from 105 to 115° C.) and the intimate dry blend is then calcined in the manner described.

In the process as described above, for example, aqueous hydrogen peroxide solutions having an $H_2O_2$ content of from 5 to 33% by weight can be used. Subsequent addition of suitable starting compounds of the other elemental constituents of the oxometallate C is advisable in particular when they are capable of catalytically decomposing the hydrogen peroxide. However, it would of course also be possible to isolate the antimony (V) oxide hydroxide from the aqueous medium and, for example, to mix it thoroughly with suitable finely divided starting compounds of the other elemental constituents of the oxometallate C and, if required, further Sb starting compounds and then to calcine this intimate mixture in the manner described.

It is important that the elemental sources of the oxometallates C are either oxides or are compounds which can be converted into oxides by heating, in the presence or absence of oxygen. In addition to the oxides, particularly suitable starting compounds are therefore halides, nitrates, formates, oxalates, acetates, carbonates and/or hydroxides (compounds such as $NH_4OH$, $(NH_4)_2CO_3$, $NH_4NO_3$, $NH_4CHO_2$, $CH_3COOH$, $NH_4CH_3CO_2$ or ammonium oxalate, which decompose and/or can be decomposed at the latest during the subsequent calcination to give compounds escaping in gaseous form, may additionally be incorporated).

In general, the thorough mixing of the starting compounds in dry or in wet form can also be carried out for the preparation of oxometallates C. If it is effected in dry form, the starting compounds are expediently used in the form of finely divided powder. Preferably, however, the thorough mixing is effected in wet form. Usually, the starting compounds are mixed with one another in the form of an aqueous solution and/or suspension. After the mixing process is complete, the fluid material is dried and is calcined after drying. Here too, the drying is preferably effected by spray drying. After calcination is complete, the oxometallates C can be comminuted again (for example by wet or dry milling, e.g. in a ball mill or by jet milling) and the particle class having a maximum particle diameter in the maximum diameter range desired for the multielement oxide (III) obtainable according to the invention can be separated from the powder obtainable thereby, and as a rule substantially comprising spherical particles, by classification (e.g. wet or dry sieving) to be carried out in a manner known per se. A preferred method of preparation of oxometallates C of the formula $(Cu, Zn)_1Sb_hH_jO_y$ comprises first converting antimony trioxide and/or $Sb_2O_4$ in an aqueous medium by means of hydrogen peroxide into a preferably finely divided, Sb (V) compound, e.g. Sb (V) oxide hydroxide hydrate, adding an ammoniacal aqueous solution of zinc carbonate and/or copper carbonate (which may have, for example, the composition $Cu_2(OH)_2CO_3$) or zinc acetate and/or copper acetate and/or zinc formate and/or copper formate to the resulting aqueous suspension, drying the resulting aqueous mixture, for example spray drying it in the manner described, and calcining the resulting powder, if required after subsequent kneading with water and subsequent extrusion and drying, in the manner described. Under advantageous conditions, the oxometallates B and the oxometallates C can be prepared in a form associated with one another. In these cases, a mixture of crystals of the oxometallates B and crystallites of the oxometallates C is obtained, which mixture can be used directly as starting material 1+2.

For the preparation of an aqueous solution required as starting material 3, starting from the abovementioned sources of the elemental constituents, it is as a rule necessary to use elevated temperatures. As a rule, temperatures of $\leq 60°$ C., in general $\leq 70°$ C., but usually $\leq 100°$ C., are used. The latter and the following apply in particular when ammonium heptamolybdate tetrahydrate [AHM=$(NH_4)_6Mo_7O_{24}.4H_2O$] is used as the Mo element source and/or ammonium metavanadate [AMV=$NH_4VO_3$] is used as the vanadium source. The conditions are particularly difficult when the element W is a component of the aqueous starting material 3 and ammonium paratungstate heptahydrate [APW=$(NH_4)_{10}W_{12}O_{41}.7H_2O$] is used in addition to at least one of the two abovementioned elemental sources as a starting compound of the relevant aqueous solution.

It has now surprisingly been found that aqueous solutions prepared at elevated temperatures as starting material 3 are usually stable during and after the subsequent cooling below the dissolution temperature, even at elemental Mo contents of $\leq 10\%$ by weight and cooling temperatures down to 20° C. or less (generally not <0° C.), based on the aqueous solution, i.e. no solid is precipitated during or after the cooling of the aqueous solution. The above statement applies as a rule also in the case of Mo contents of up to 20% by weight, on the same basis. The same applies for V and W.

Usually, the Mo content of such aqueous solutions cooled to 20° C. or less (generally not below 0° C.) and suitable as starting material 3 is not more than 35% by weight, based on the solutions.

The above finding is due to the fact that the dissolution at elevated temperatures evidently results in compounds of the relevant elements which have higher water solubility. This concept is supported by the fact that the residue obtainable from such an aqueous solution by drying (e.g. spray drying) also has a correspondingly higher solubility (even at the correspondingly low temperatures) in water.

An expedient procedure is therefore as follows. At a temperature $T_L \geq 60°$ C. (for example at up to 65° C. or at up to 75° C. or at up to 85° C. or at up to 95° C. or $\leq 100°$ C.), an aqueous solution suitable as starting material 3 is produced. The finely divided solid starting materials 1, 2 are then incorporated into this aqueous solution after cooling to a temperature $T_E<T_L$. Frequently, $T_L$ is $\geq 70°$ C. and $T_E$ is $\leq 70°$ C. If slightly lower dissolution rates and lower solids contents are accepted, however, $T_L \leq 60°$ C. is also possible.

The incorporation of the prepared solid starting materials 1, 2 into the aqueous starting material 3 (aqueous solution or aqueous suspension or material kneaded to a paste with water) is usually effected by addition of the starting materials 1, 2 to the aqueous starting material 3 cooled as stated above and subsequent mechanical mixing, for example with the use of stirring or dispersing aids, over a period of from a few minutes to hours, preferably from 20 to 40 minutes. As stated above, it is particularly advantageous according to the invention if the incorporation of the solid starting materials 1, 2 into the aqueous starting material 3 is effected at $\leq 70°$ C., preferably $\leq 60°$ C., particularly preferably $\leq 40°$ C. As a rule, the incorporation temperature is $\leq 0°$ C.

It is furthermore advantageous if the solid starting materials 1, 2 are incorporated into an aqueous starting material 3 whose pH at 25° C. is from 4 to 7, preferably from 5 to 6.5. The latter can be achieved, for example, by adding one or more pH buffer systems to the aqueous starting material 3. For example, the addition of ammonia and acetic acid and/or formic acid or the addition of ammonium acetate and/or ammonium formate is suitable as such buffer systems. Of course, ammonium carbonate may also be concomitantly used for the abovementioned purpose. The drying of the aqueous mixture obtained on incorporation of the starting materials 1, 2 into the aqueous starting material 3 is usually effected by spray drying. Advantageously, outlet temperatures of from 100 to 150° C. are established. As always in this document, spray drying can be effected either cocurrently or countercurrently.

Our own investigations have shown that, in the novel thermal treatment of the intimate dry blend containing the starting materials 1, 3 and, if required, 2, the structure type of the crystallites contained in the starting materials 1, 2 is substantially retained or at most is transformed into other structure types. However, fusion (dissolution in one another) of the components of the starting materials 1, 2 with one another or with those of the starting material 3 substantially does not take place.

As indicated above, this opens up the possibility of separating off the particle class having a maximum diameter desired for the multielement oxide material (III) (as a rule from >0 to 300 μm, preferably from 0.01 to 100 μm, particularly preferably from 0.05 to 20 μm) by classification to be carried out in a manner known per se (for example wet or dry sieving), after milling of the preformed starting materials 1, 2, and thus of using it tailored-made for the preparation of the desired multielement oxide material.

In principle, the multielement oxide materials III obtainable according to the invention, and also the multielement oxide active materials I, II obtainable according to the invention, can be used in powder form as catalysts for the heterogeneously catalyzed partial gas-phase oxidation of acrolein to acrylic acid (for example, in a fluidized bed or fluidized bed reactor).

As in the case of the multielement oxide active materials I, II, however, the multielement oxide active materials III are also used, preferably after shaping into moldings having a certain geometry, as catalysts for the abovementioned partial oxidation. The shaping and choice of the geometry can be carried out as described above for the multielement oxide active materials I, II.

This means that either the intimate dry blend still to be subjected to the thermal treatment according to the invention or the multielement oxide active material III itself, obtained according to the invention therefrom, can be applied to premolded inert catalyst supports. In the former case, the novel thermal treatment is carried out after coating of the catalyst supports is complete. Application to the catalyst support is preferably effected after the novel thermal treatment.

The conventional support materials, such as porous or nonporous aluminas, silica, thorium dioxide, zirconium dioxide, silicon carbide or silicates, such as magnesium silicate or aluminum silicate, can be used. The supports may have a regular or irregular shape, supports having a regular shape and substantial surface roughness, for example spheres or hollow cylinders, being preferred. For example, the use of substantially nonporous, spherical steatite supports which have a rough surface and whose diameter is from 1 to 8 mm, preferably from 4 to 5 mm, is suitable. The coat thickness of the active material is expediently chosen to be in the range from 50 to 500 µm, preferably from 150 to 250 µm. However, as described above, hollow cylinders (rings) can also be used as supports. It should be pointed out here that, for the coating of the supports in the preparation of such coated catalysts, the powder material to be applied or the support is as a rule moistened with binder and, after the application, is dried again, for example by means of hot air.

For the preparation of the coated catalysts, the coating of the supports is carried out as a rule in a suitable container, as disclosed, for example, in DE-A 29 096 71 or in EP-A 293 859. Coating and shaping are preferably effected as described in EP-A 714700.

The novel process can be applied in a suitable manner in such a way that the resulting multielement oxide active materials (III) have a specific surface area of from 0.50 to 150 $m^2/g$, a specific pore volume of from 0.10 to 0.90 $cm^3/g$ and a pore diameter distribution such that at least 10% of the total pore volume are in each of the diameter ranges from 0.1<1 µm, from 1.0 to <10 µm and from 10 to 100 µm. The pore diameter distributions stated as being preferred in EP-A 293 859 can also be established.

Of course, the novel multielement oxide materials (III) can also be operated as unsupported catalysts. In this respect, the intimate dry blend comprising starting materials 1, 2 and 3 is preferably compacted directly to give the desired catalyst geometry (for example by means of tableting or extrusion in a screw extruder or ram extruder), it being possible, if required, to add assistants known per se, e.g. graphite or stearic acid as lubricants and/or molding assistants and reinforcing agents, such as microfibers of glass, asbestos, silicon carbide or potassium titanate, and is subjected to the thermal treatment according to the invention. Here too, the thermal treatment according to the invention can in general be effected before the shaping. Preferred unsupported catalyst geometries are hollow cylinders having an external diameter and a length of from 2 to 10 mm or from 3 to 8 mm and a wall thickness of from 1 to 3 mm.

The multielement oxide active materials obtainable according to the invention are particularly suitable for catalysts having high activity and selectivity (for a specified conversion) for the gas-phase catalytic oxidation of acrolein to acrylic acid. Acrolein which was produced by the catalytic gas-phase partial oxidation of propene is usually used in the process. As a rule, the acrolein-containing reaction gases of this propene oxidation are used without intermediate purification. Usually, the gas-phase catalytic partial oxidation of the acrolein is carried out in tube-bundle reactors as a heterogeneous fixed-bed oxidation. Oxygen, expediently diluted with inert gases (e.g. in the form of air), is used as an oxidizing agent in a manner known per se. Suitable diluent gases are, for example, $N_2$, $CO_2$, hydrocarbon, recycled reaction exit gases and/or steam. As a rule, an acrolein:oxygen:steam:inert gas volume ratio of 1:(1 to 3):(0 to 20):(3 to 30), preferably of 1:(1 to 3):(0.5 to 10):(7 to 18), is established in the acrolein partial oxidation. The reaction pressure is generally from 1 to 3 bar and the total space velocity is preferably from 1 000 to 3 500 l(S.T.P.) per l per h. Typical multi-tube fixed-bed reactors are described, for example, in. DE-A 2830765, DE-A 2201528 or U.S. Pat. No. 3,147,084. The reaction temperature is usually chosen so that the acrolein conversion in a single pass is above 90%, preferably above 98%. In this respect, reaction temperatures of from 230 to 330° C. are usually required.

The multielement oxide active materials according to the invention and the catalysts containing them are particularly suitable for the high-load procedure described in WO 00/53557 and in DE-A 19910508. However, they are also suitable for the processes of DE-A 10313214, DE-A 10313213, DE-A 10313211, DE-A 10313208 and 10313209.

In addition to the gas-phase catalytic partial oxidation of acrolein to acrylic acid, the novel products of the process are, however, also capable of catalyzing the gas-phase catalytic partial oxidation of other organic compounds, in particular other alkanes, alkanols, alkanals, alkenes and alkenols, preferably of 3 to 6 carbon atoms (e.g. propylene, methacrolein, tert-butanol, methyl ether of tert-butanol, isobutene, isobutane or isobutyraldehyde), to give olefinically unsaturated aldehydes and/or carboxylic acids, and the corresponding nitriles (ammoxidation, especially of propene to acrylonitrile and of isobutene or tert-butanol to methacrylonitrile). The preparation of acrolein, methacrolein and methacrylic acid may be mentioned by way of example. However, they are also suitable for the oxidative dehydrogenation of paraffinic or olefinic compounds.

In principle, a wide range of oven types, e.g. tray ovens, rotary tube furnaces, belt calciners, fluidized-bed ovens or shaft furnaces, are suitable for carrying out the novel thermal treatment and for carrying out the calcinations in the preparation of the starting materials 1 and 2. According to the invention, rotary tube furnaces are preferably suitable for this purpose.

EXAMPLE

1. General Description of the Rotary Tube Furnace Used for the Novel Thermal Treatment and for the Calcination in the Preparation of Starting Materials 1 and 2

A schematic diagram of the rotary tube furnace is shown in FIG. 1 attached to this document. The reference numerals below relate to this FIG. 1.

The central element of the rotary tube furnace is the rotary tube (1). It is 4 000 mm long and has an internal diameter of 700 mm. It is produced from stainless steel 1.4893 and has a wall thickness of 10 mm.

Reciprocating lances which have a height of 5 cm and a length of 23.5 cm are mounted on the inner surface of the rotary tube furnace. They serve primarily for lifting and thus thoroughly mixing the material to be thermally treated in the rotary tube furnace.

Four reciprocating lances (a quadruple) are mounted in each case equidistant (in each case 90° spacing) around the circumference at one and the same height of the rotary tube furnace. Eight such quadruples (spacing of 23.5 cm in each case) are located along the rotary tube furnace. The reciprocating lances of two adjacent quadruples are arranged staggered relative to one another on the circumference. No reciprocating lances are present at the beginning and at the end of the rotary tube furnace (first and last 23.5 cm).

The rotary tube rotates freely in a right parallelepiped (2) which has four equally long, electrically heated (resistance heating) heating zones which follow one another along the length of the rotary tube and each of which surrounds the circumference of the rotary tube furnace. Each of the heating zones can heat the corresponding rotary tube section to temperatures of from room temperature to 850° C. The maximum heating power of each heating zone is 30 kW. The distance between the electrical heating zone and the outer surface of the rotary tube is about 10 cm. At the beginning and at the end, the rotary tube projects about 30 cm out of the right parallelepiped.

The speed may be varied from 0 to 3 revolutions per minute. The rotary tube can be rotated both counterclockewise and clockwise. In the case of clockwise rotation, the material remains in the rotary tube; in the case of counter-clockwise rotation, the material is transported from the feed (3) to the discharge (4). The angle of inclination of the rotary tube relative to the horizontal may be varied from 0° to 2°. In batchwise operation, it is in fact 0°. In continuous operation, the lowest point of the rotary tube is at the material discharge. Rapid cooling of the rotary tube can be effected by switching off the electrical heating zones and switching on a fan (5). This aspirates ambient air through holes (6) present in the lower base of the right parallelepiped and transports said air through three flaps (7) present in the cover and having a variable orifice.

The material feed is controlled by means of a rotary vane feeder (mass control). As stated above, the material discharge is controlled by means of the direction of rotation of the rotary tube.

During batchwise operation of the rotary tube, an amount of from 250 to 500 kg of material can be thermally treated. It is usually present exclusively in the heated part of the rotary tube.

From a lance (8) located on the central axis of the rotary tube, a total of three thermocouples (9) lead vertically into the material at intervals of 800 mm. They permit the determination of the temperature of the material. In this document, the temperature of the material is understood as meaning the arithmetic mean of the three thermocouple temperatures. Within the material present in the rotary tube the maximum deviation of two measured temperatures is, according to the invention, expediently less than 30° C., preferably less than 20° C., particularly preferably less than 10° C., very particularly preferably less than 5 or 3° C.

Gas streams by means of which the calcination atmosphere or in general the atmosphere of the thermal treatment of the material is adjustable can be passed through the rotary tube.

The heater (10) makes it possible to heat the gas stream passed into the rotary tube, prior to its entry into the rotary tube, to the desired temperature (e.g. to the temperature desired for the material in the rotary tube). The maximum power of the heater is 1×50 kW+1×30 kW. In principle, the heater (10) may be, for example, an indirect heat exchanger. Such a heater can in principle also be used as a cooler. As a rule, however, it is an electric heater in which the gas stream is passed over electrically heated metal wires (expediently CSN flow heater, type 97D/80 from C. Schniewindt KG, 58805 Neuerade, Germany).

In principle, the rotary tube apparatus provides the possibility of partly or completely circulating the gas stream passed through the rotary tube. The circulation pipe required for this purpose is movably connected to the rotary tube at the rotary tube inlet and at the rotary tube outlet via ball bearings or via press-fit graphite seals. These connections are flushed with inert gas (e.g. nitrogen) (sealing gas). The two flushing streams (11) supplement the gas stream passed through the rotary tube at the inlet into the rotary tube and at the outlet from the rotary tube. Expediently, the rotary tube tapers at its beginning and at its end and projects into the entering or departing tube of the circulation pipe.

Downstream of the outlet of the gas stream passed through the rotary tube is a cyclone (12), for separating off solid particles entrained with the gas stream (the centrifugal separator separates off solid particles suspended in the gas phase, by cooperation of centrifugal and gravitational forces; the centrifugal force of the gas stream rotating as a vortex accelerates the sedimentation of the suspended particles).

The recycle gas (24) (the gas circulation) is transported by means of a recycle gas compressor (13) (fan) which aspirates in the direction of the cyclone and applies pressure in the other direction. Immediately downstream of the recycle gas compressor, the gas pressure is as a rule above one atmosphere. A recycle gas outlet (recycle gas can be discharged via a control valve (14)) is located downstream of the recycle gas compressor. An aperture present downstream of the outlet (cross-sectional tapering by about a factor of 3, pressure reducer) (15) facilitates the outlet. The pressure downstream of the rotary tube exit can be regulated by means of the control valve. This is effected in cooperation with a pressure sensor (16) mounted downstream of the rotary tube exit, the exit gas compressor (17) (fan), which aspirates in the direction of the control valve, the recycle gas compressor (13) and the fresh gas feed. The pressure (directly) downstream of the rotary tube exit can be adjusted to be, for example, up to +1.0 mbar above and, for example, up to −1.2 mbar below the external pressure. This means that the pressure of the gas stream flowing through the rotary tube can be below the ambient pressure of the rotary tube on leaving the rotary tube.

If it is not intended to circulate, even at least proportionately, the gas stream passed through the rotary tube, the connection between cyclone (12) and recycle gas compressor (13) is closed according to the three-way valve principle (26) and the gas stream is passed directly into the exit gas purification apparatus (23). In this case, the connection to the exit gas purification apparatus is likewise closed according to the three-way valve principle, said connection being present downstream of the recycle gas compressor. If the gas stream substantially comprises air, the latter is in this case aspirated (27) via the recycle gas compressor (13). The connection to the cyclone is closed according to the three-way valve principle. In this case, the gas stream is preferably sucked through the rotary tube so that the internal pressure of the rotary tube is less than the ambient pressure.

During continuous operation of the rotary tube furnace apparatus, the pressure downstream of the rotary tube exit is advantageously adjusted to be −0.2 mbar below the external pressure. During batchwise operation of the rotary tube apparatus, the pressure downstream of the rotary tube exit is advantageously adjusted to be −0.8 mbar below the external pressure. The slightly reduced pressure serves the purpose of avoiding contamination of the ambient air with gas mixture from the rotary tube furnace.

Sensors (18) which, for example, determine the ammonia content and the oxygen content in the recycle gas are present between the recycle gas compressor and the cyclone. The ammonia sensor preferably operates according to an optical measuring principle (the absorption of light of certain wavelength is proportional to the ammonia content of the gas) and is expediently an apparatus of the type MCS 100 from Perkin & Elmer. The oxygen sensor is based on the paramagnetic properties of oxygen and is expediently an oxygen sensor of the type Oxymat MAT SF 7 MB1010-2CA01-1AA1-Z from Siemens.

Between the aperture (15) and the heater (10), gases, such as air, nitrogen, ammonia or other gases, can be metered to the actually recirculated recycle gas fraction (19). Frequently, a base load of nitrogen is metered in (20). Using a separate nitrogen/air splitter (21), it is possible to respond to the measured value of the oxygen sensor.

The discharged recycle gas fraction (22) (exit gas) frequently contains gases which are not completely safe, such as $NO_x$, acetic acid, $NH_3$, etc.), and these are therefore usually separated off (23) in an exit gas purification apparatus.

For this purpose, the exit gas is as a rule first passed via a scrubber column (substantially a column which is free of internals and contains a packing having separation activity upstream of its exit; the exit gas and aqueous spray mist are passed cocurrently and countercurrently (two spray nozzles having opposite spraying directions)).

On arriving from the scrubber column, the exit gas is passed into an apparatus which contains a fine dust filter (as a rule a bundle of tube filters), from the interior of which the penetrated exit gas is removed. Finally, incineration is effected in a muffle furnace.

The amount of the gas stream which differs from the sealing gas and is fed to the rotary tube is measured and regulated by means of a sensor (28) of the type Model 455 Jr from KURZ Instruments, Inc., Montery (USA) (measuring principle: thermal convective mass flow measurement using an equal-temperature anenometer).

During continuous operation, material and gas phase are passed countercurrently through the rotary tube furnace.

In connection with this example, nitrogen always means nitrogen having a purity of >99% by volume.

2. Preparation of the Starting Material 1 (Phase B) Having the Stoichiometry $Cu_1Mo_{0.5}W_{0.5}O_4$ 98 l of a 25% strength by weight aqueous $NH_3$ solution were added to 603 l of water. 100 kg of copper(II) acetate hydrate (content: 40.0% by weight of CuO) were then dissolved in the aqueous mixture, resulting in a clear, deep blue aqueous solution 1 which contained 3.9% by weight of Cu and was at room temperature.

Independently of the solution 1, 620 l of water were heated to 40° C. 27.4 kg of ammonium heptamolybdate tetrahydrate (81.5% by weight of $MoO_3$) were dissolved therein in the course of 20 minutes with stirring while maintaining the 40° C. Thereafter, 40.4 kg of ammonium paratungstate heptahydrate (88.9% by weight of $WO_3$) were added, and after heating to 90° C. in the course of 45 minutes, were dissolved at this temperature with stirring. A clear, yellow-orange aqueous solution 2 was obtained.

The aqueous solution 1 was then stirred into the solution 2 which was at 90° C., the temperature of the total mixture not falling below 80° C. The resulting aqueous suspension was stirred for a further 30 minutes at 80° C. It was then spray dried using a spray dryer of the type S-50-N/R from Niro-Atomizer (Copenhagen) (gas inlet temperature: 315° C., gas outlet temperature: 110° C., cocurrent). The spray-dried powder had a particle diameter of from 2 to 50 µm.

100 kg of light-green spray-dried powder thus obtained were metered into a kneader of the type VIU 160 (sigma blades) from AMK (Aachener Misch-und Knetmaschinen Fabrik) and kneaded with addition of 8 l of water (residence time: 30 minutes, temperature: from 40 to 50° C.). Thereafter, the kneaded material was emptied into an extruder and shaped into extrudates (length: 1-10 cm; diameter: 6 mm) by means of the extruder (from Bonnot Company (Ohio), type: G 103-10/D7A-572K (6" extruder W/Packer)). The extrudates were dried on a belt dryer for 1 hour at 120° C. (material temperature). The dried extrudates were then subjected to the thermal treatment (calcination) in the rotary tube furnace described under 1., as follows:

the thermal treatment was effected continuously with a material feed of 50 kg/h of extrudates;
the angle of inclination of the rotary tube relative to the horizontal was 2°;
an air stream of 75 m³(S.T.P.)/h was passed through the rotary tube countercurrently to the material, said air stream being supplemented by a total of (2×25) 50 m³(S.T.P.)/h of sealing gas at 25° C.;
the pressure downstream of the rotary tube exit was 0.8 mbar below the external pressure;
the rotary tube rotated counterclockwise at 1.5 revolutions per minute;
no recycle gas procedure was used;
during the first pass of the extrudates through the rotary tube, the temperature of the outer surface of the rotary tube was brought to 340° C. and the air stream was passed at from 20 to 30° C. into the rotary tube;
the extrudates were then passed through the rotary tube with the same throughput and, apart from the following differences, under the same conditions:
the temperature of the rotary tube wall was brought to 790° C.;
the air stream was heated to 400° C. before being passed into the rotary tube.

The extrudates having a red-brown color were then milled on a biplex cross-flow classifying mill (BQ 500) from Hosokawa-Alpine (Augsburg) to a mean particle diameter of from 3 to 5 µm. The starting material 1 thus obtained had a BET surface area of ≦1 m²/g. The following phases were determined by means of X-ray diffraction:
1. $CuMoO_4$-III having the wolframite structure;
2. HT copper molybdate.

3. Preparation of the Starting Material 2 (Phase C) Having the Stoichiometry $CuSb_2O_6$ 52 kg of antimony trioxide (99.9% by weight of $Sb_2O_3$) were suspended in 216 l of water (25° C.) with stirring. The resulting aqueous suspension was heated to 80° C. Stirring was then effected for a further 20 minutes while maintaining the 80° C. 40 kg of 30% strength by weight aqueous hydrogen peroxide solution were then added in the course of one hour, the 80° C. being maintained. While maintaining this temperature, stirring was effected for a further 1.5 hours. Thereafter, 20 l of water at 60° C. were added and an aqueous suspension 1 was thus obtained. 618.3 kg of an aqueous ammoniacal copper(II) acetate solution (60.8 g of copper acetate per kg of solution and 75 l of a 25% strength by weight aqueous ammonia solution in the 618.3 kg of solution) were stirred into said suspension 1 at 70° C. Thereafter, heating was effected to 95° C. and stirring was effected at this temperature for a further 30 minutes. 50 l of water at 70° C. were then added and the mixture was heated to 80° C.

Finally, the aqueous suspension was spray dried (spray dryer of the type S-50-N/R from Niro-Atomizer (Copenhagen), gas inlet temperature 360° C., gas outlet temperature 110° C., cocurrent). The spray-dried powder had a particle diameter of from 2 to 50 µm.

75 kg of spray-dried powder thus obtained were metered into a kneader of the type VIU 160 (sigma blades) from AMK (Aachener Misch-und Knetmaschinen Fabrik) and kneaded with addition of 12 l of water (residence time: 30 minutes, temperature from 40 to 50° C.). Thereafter, the kneaded material was emptied into an extruder (same extruder as in the preparation of phase B) and shaped by means of the extruder to give extrudates (length 1-10 cm; diameter 6 mm). The extrudates were dried on a belt dryer for 1 hour at 120° C. (material temperature).

250 kg of extrudates thus obtained were subjected to the thermal treatment (calcination) in the rotary tube furnace described under 1., as follows:
the thermal treatment was effected batchwise with an amount of 250 kg of material;
the angle of inclination of the rotary tube relative to the horizontal was ≈0°;

the rotary tube rotated clockwise at 1.5 revolutions per minute;

a gas stream of 205 m³(S.T.P.)/h was passed through the rotary tube; at the beginning of the thermal treatment, said gas stream consisted of 180 m³(S.T.P.)/h of air and 1×25 m³(S.T.P.)/h of $N_2$ as sealing gas; the gas stream leaving the rotary tube was supplemented with a further 1×25 m³(S.T.P.)/h of $N_2$; 22-25% by volume of this total stream were recycled into the rotary tube and the remainder discharged; the amount discharged was supplemented by the sealing gas and, as the residual amount, by fresh air;

the gas stream was passed at 25° C. into the rotary tube;

the pressure downstream of the rotary tube exit was 0.5 mbar below external pressure (atmospheric pressure);

the temperature in the material was initially increased in the course of 1.5 hours linearly from 25° C. to 250° C.; the temperature in the material was then increased in the course of 2 hours linearly from 250° C. to 300° C. and this temperature was maintained for 2 hours; thereafter, the temperature in the material was increased linearly in the course of 3 hours from 300° C. to 405° C. and this temperature was then maintained for 2 hours; thereafter, the heating zones were switched off and, by activating the rapid cooling of the rotary tube by aspirating air, the temperature inside the material was reduced in the course of 1 hour to a temperature below 100° C. and finally to ambient temperature.

The resulting starting material 2 in powder form had a specific BET surface area of 0.6 m²/g and the composition $CuSb_2O_6$. The powder X-ray pattern of the powder obtained exhibited substantially the reflections of $CuSb_2O_6$ (comparative spectrum 17-0284 of the JCPDS-ICDD Index).

4. Preparation of the Starting Material 3 Having the Stoichiometry $Mo_{12}V_{3.35}W_{1.38}$ 900 l of water were initially taken in a stirred kettle at 25° C. with stirring. Thereafter, 122.4 kg of ammonium heptamolybdate tetrahydrate (81.5% by weight of $MoO_3$) were added and heating was effected to 90° C. with stirring. Thereafter, first 22.7 kg of ammonium metavanadate and finally 20.0 kg of ammonium paratungstate heptahydrate (88.9% by weight of $WO_3$) were stirred in while maintaining the 90° C. By stirring for 80 minutes altogether at 90° C., a clear orange-colored solution was obtained. This was cooled to 80° C. Thereafter, first 18.8 kg of acetic acid (≈100% strength by weight, glacial acetic acid) and then 24 l of 25% strength by weight aqueous ammonia solution were stirred in while maintaining the 80° C.

The solution remained clear and orange-colored and was spray dried using a spray dryer of the type S-50-N/R from Niro-Atomizer (Copenhagen) (gas inlet temperature: 260° C., gas outlet temperature: 110° C., cocurrent). The resulting spray-dried powder formed the starting material 3 and had a particle diameter of from 2 to 50 μm.

5. Preparation of the Dry Material to be Thermally Treated According to the Invention and Having the Stoichiometry $(Mo_{12}V_{3.46}W_{1.39})_{0.87}(CuMo_{0.5}W_{0.5}O_4)_{0.4}(CuSb_2O_6)_{0.4}$ In a trough kneader of the type VIU 160 from AMK (Aachener Misch-und Knetmaschinen Fabrik) having two sigma blades, 75 kg of starting material 3, 5.2 l of water and 6.9 kg of acetic acid (100% by weight of glacial acetic acid) were initially taken and kneaded for 22 minutes. Thereafter, 3.1 kg of starting material 1 and 4.7 kg of starting material 2 were added and were kneaded for a further 8 minutes (T=40 to 50° C.).

Thereafter, the kneaded material was emptied into an extruder (same extruder as in the preparation of phase B) and shaped by means of the extruder to give extrudates (from 1 to 10 cm length, 6 cm diameter). These were dried on a belt dryer for 1 hour at a temperature (material temperature) of 120° C.

306 kg of the dried extrudates were then subjected to the thermal treatment in a rotary tube furnace described under 1., as follows:

the thermal treatment was effected batchwise with 306 kg of material;

the angle of inclination of the rotary tube relative to the horizontal was ≈0°;

the rotary tube rotated clockwise at 1.5 revolutions per minute;

the material temperature was first increased in the course of 2 hours substantially linearly from 25° C. to 100° C.;

during this time, 205 m³(S.T.P.)/h of a stream (substantially) comprising nitrogen was passed through the rotary tube. In the steady state (after displacement of the air originally contained), said nitrogen stream had the following composition:
110 m³(S.T.P.)/h of base load–nitrogen (20),
25 m³(S.T.P.)/h of sealing gas–nitrogen (11) and
70 m³(S.T.P.)/h of recirculated gas (19).

The nitrogen sealing gas was fed in at 25° C. The mixture of the other two nitrogen streams was passed in each case into the rotary tube at the temperature which the material had in each case in the rotary tube.

the material temperature was then increased from 100° C. to 320° C. at a heating rate of 0.7° C./min;

a gas stream of 205 m³(S.T.P.)/h which had the following composition was passed through the rotary tube until a material temperature of 300° C. was reached:
110 m³(S.T.P.)/h consisting of a base load–nitrogen (20) and gases liberated in the rotary tube,
25 m³(S.T.P.)/h of sealing gas–nitrogen (11) and
70 m³(S.T.P.)/h of recirculated gas (19).

The nitrogen sealing gas was fed in at 25° C. The mixture of the other two gas streams was passed in each case into the rotary tube at the temperature which the material in the rotary tube had in each case.

From the time of exceeding the material temperature of 160° C. until reaching a material temperature of 300° C., 40 mol % of the amount $M^A$ of ammonia liberated altogether in the course of the entire thermal treatment of the material were liberated from the material.

on reaching the material temperature of 320° C., the oxygen content of the gas stream fed to the rotary tube was increased from 0% by volume to 1.5% by volume and maintained over the subsequent 4 hours.

At the same time, the temperature prevailing in the four heating zones heating the rotary tube was reduced by 5° C. (to 325° C.) and thus maintained during the subsequent 4 hours.

The material temperature passed through a temperature maximum which was above 325° C. and did not exceed 340° C., before the material temperature was reduced again to 325° C.

The composition of the 205 m³(S.T.P.)/h gas stream passed through the rotary tube was changed as follows during this period of 4 hours.
95 m³(S.T.P.)/h consisting of base load–nitrogen (20) and gases liberated in the rotary tube;

25 m³(S.T.P.)/h of sealing gas–nitrogen (11);
70 m³(S.T.P.)/h of recirculated gas and
15 m³(S.T.P.)/h of air via the splitter (21).
The nitrogen sealing gas was fed in at 25° C.
The mixture of the other gas streams was fed into the rotary tube in each case at the temperature which the material in the rotary tube had in each case.
From the time of exceeding the material temperature of 300° C. until 4 hours had elapsed, 55 mol % of the amount $M^4$ of ammonia liberated altogether in the course of the entire thermal treatment of the material were liberated from the material (thus, altogether 40 mol %+55 mol %=95 mol % of the amount $M^4$ of ammonia were liberated until 4 hours had elapsed).
with the elapse of 4 hours, the temperature of the material was increased to 400° C. at a heating rate of 0.85° C./min in the course of about 1.5 hours.
This temperature was then maintained for 30 minutes.
The composition of the 205 m³(S.T.P.)/h gas stream fed to the rotary tube was as follows during this time:
  95 m³(S.T.P.)/h composed of base load–nitrogen (20) and gases liberated in the rotary tube;
  15 m³(S.T.P.)/h of air (splitter (21));
  25 m³(S.T.P.)/h of nitrogen sealing gas (11) and
  70 m³(S.T.P.)/h of recirculated gas.
The nitrogen sealing gas was fed in at 25° C. The mixture of the other gas streams was passed into the rotary tube in each case at the temperature which the material in the rotary tube had in each case.
the calcination was terminated by reducing the temperature of the material; for this purpose, the heating zones were switched off and the rapid cooling of the rotary tube was switched on by aspirating air, and the material temperature was reduced to a temperature below 100° C. in the course of 2 hours and finally reduced to ambient temperature;
on switching off the heating zones, the composition of the 205 m³(S.T.P.)/h gas stream fed to the rotary tube was changed to the following mixture:
  110 m³(S.T.P.)/h composed of base load–nitrogen (20) and gases liberated in the rotary tube;
  0: m³(S.T.P.)/h of air (splitter (21));
  25 m³(S.T.P.)/h of nitrogen sealing gas (11) and
  70 m³(S.T.P.)/h of recirculated gas.
The gas stream was fed to the rotary tube at 25° C.
during the entire thermal treatment, the pressure (directly) downstream of the rotary tube exit was 0.2 mbar below the external pressure.

6. Shaping of the Multimetal Oxide Active Material

Figure 2:
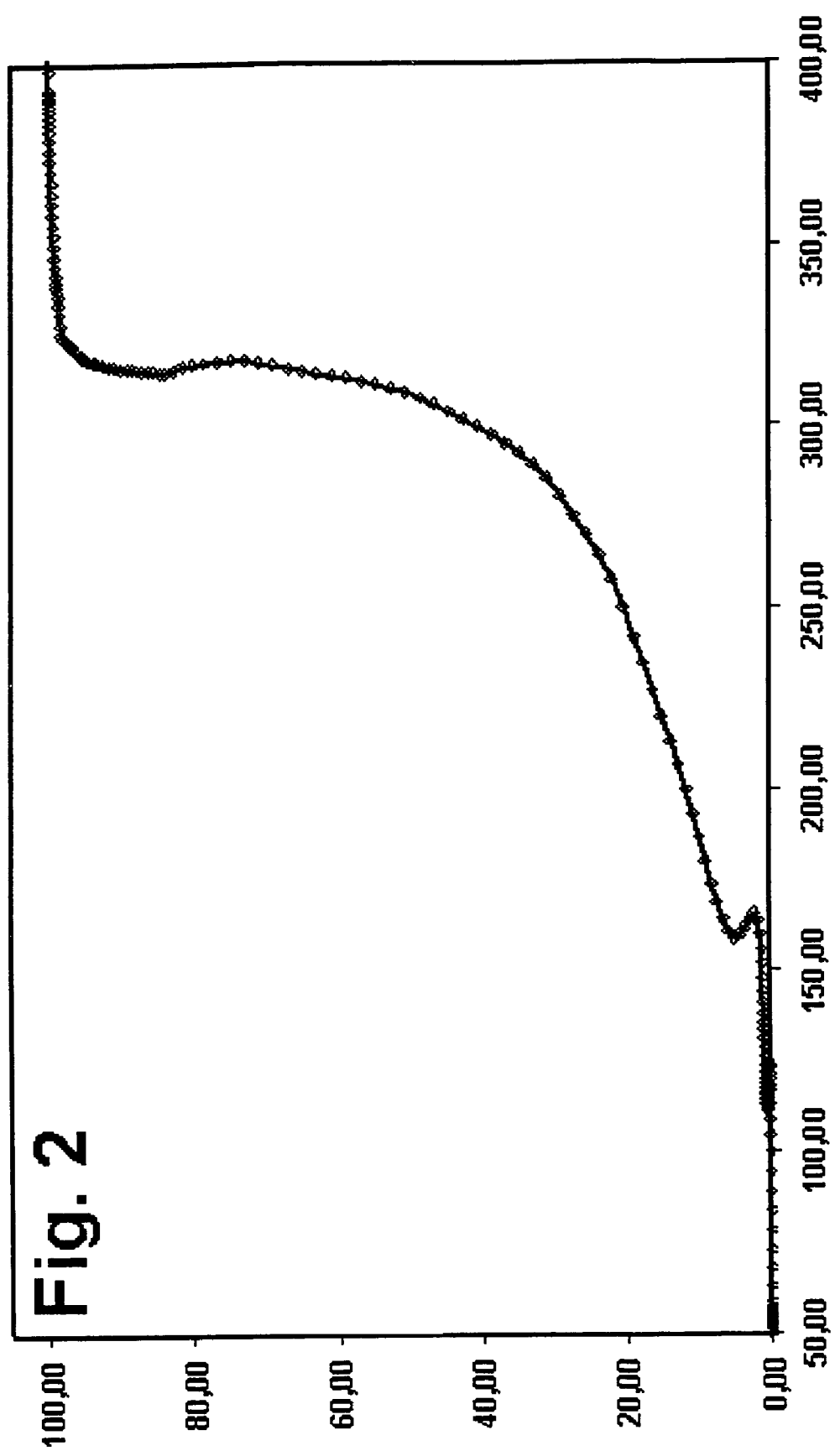
FIG. 2 shows the percentage of $M^4$ as a function of the material temperature in ° C.
Figure 3:
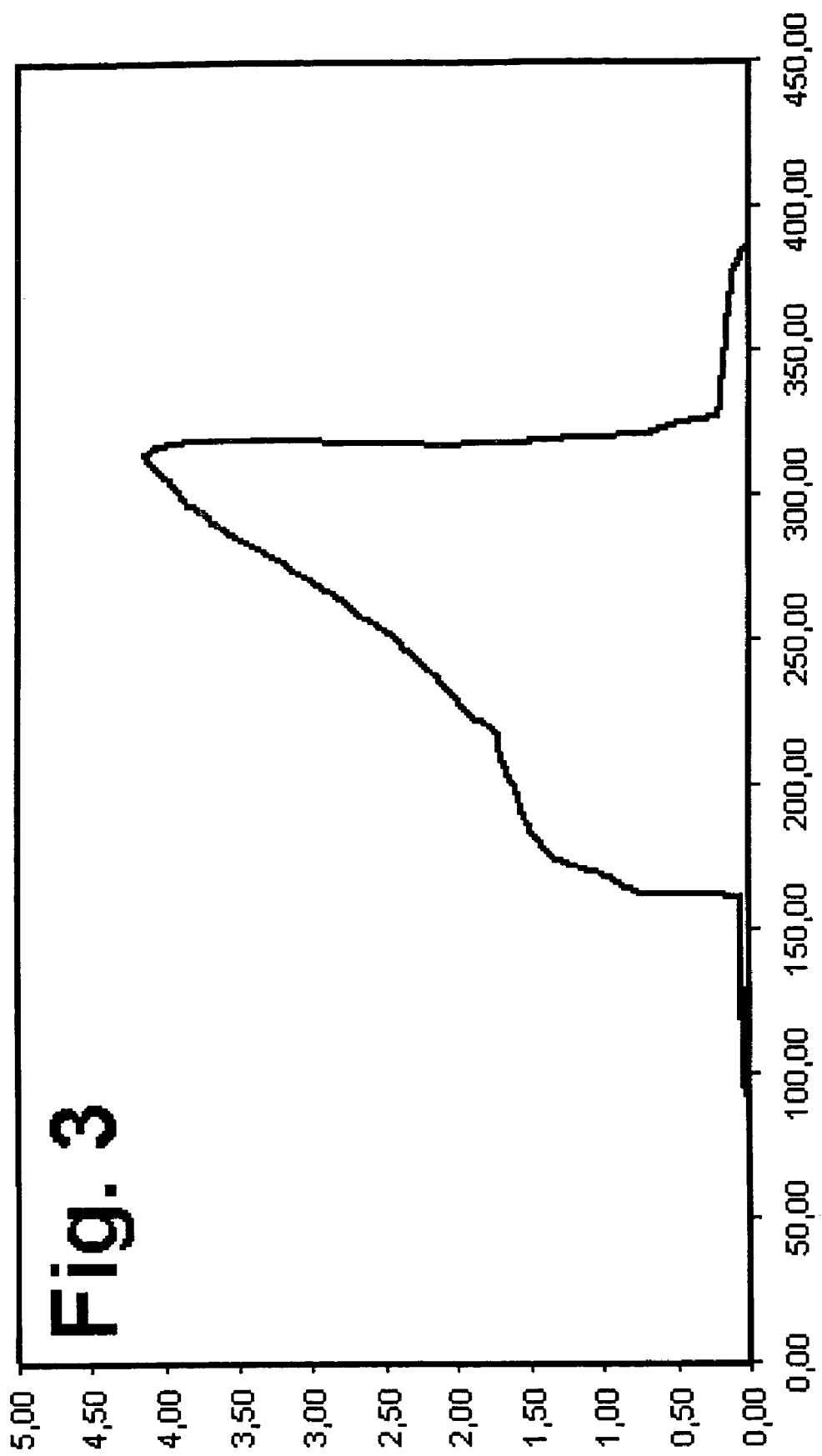
FIG. 3 shows the ammonia concentration of the atmosphere A in % by volume over the thermal treatment as a function of the material temperature in ° C.

The catalytically active material obtained in 5. was milled by means of a biplex cross-flow classifying mill (BQ 500) (from Hosokawa-Alpine Augsburg) to a finely divided powder, 50% of whose particles passed through a sieve of mesh size from 1 to 10 μm and whose fraction of particles having maximum dimensions above 50 μm was less than 1%. The specific surface area of the multimetal oxide active material powder was . . . cm²/g.
Annular supports (7 mm external diameter, 3 mm length, 4 mm internal diameter, steatite of the type C220 from CeramTec having a surface roughness Rz of 45 μm) were coated by means of the milled powder as in S1 of EP-B 714700. The binder was an aqueous solution of 75% by weight of water and 25% by weight of glycerol.
However, in contrast to the abovementioned example S1, the active material fraction of the resulting coated catalysts was chosen to be 20% by weight (based on the total weight of support and active material). The ratio of powder to binder was adjusted proportionally.
FIG. 2 shows the percentage of $M^4$ as a function of the material temperature in ° C. FIG. 3 shows the ammonia concentration of the atmosphere A in % by volume over the thermal treatment as a function of the material temperature in ° C.

7. Testing of the Coated Catalysts

The coated catalysts were tested as follows in a model catalyst tube around which a salt bath (mixture of potassium nitrate and sodium nitrate) flowed:
Model catalyst tube: V2A stainless steel, 2 mm wall thickness, 26 mm internal diameter, a centered thermal sleeve (for receiving a thermocouple) of 4 mm external diameter, 1.56 l of the free model catalyst tube space were filled with the coated catalyst.
The reaction gas mixture had the following starting composition:
  4.8% by volume of acrolein, 7% by volume of oxygen, 10% by volume of steam and 76% by volume of nitrogen, the remaining amount comprising a mixture of oxides of carbon and oxygenates of propylene.
The model catalyst tube was loaded with 2 800 l(S.T.P.)/h of reaction starting mixture. The temperature of the salt bath was adjusted so that an acrolein conversion of 99.3 mol % resulted during a single pass.
The salt bath temperature T required in this respect was 262° C. and the selectivity of the acrylic acid formation was 96.4 mol % of acrylic acid.
At this point, it should also be stated that, with these coated catalysts, regular loading of tube-bundle reactors having from 5000 to 40 000 catalyst tubes (wall thickness typically from 1 to 3 mm, internal diameter as a rule from 20 to 30 mm, frequently from 21 to 26 mm, length typically from 2 to 4 m) is possible, which loading is such that, owing to the homogeneous preparation of the active material, in a random sample of 12 catalyst tubes the difference between the arithmetic mean activity and the highest or lowest activity is not more than 8° C., frequently not more than 6° C., often not more than 4° C. and in advantageous cases not more than 2° C.
A measure used for the activity of the catalyst tube loading is the temperature which a salt bath (mixture of 53% by weight of potassium nitrate, 40% by weight of sodium nitrite and 7% by weight of sodium nitrate) flowing around the individual catalyst tube must have in order that, in a single pass of reaction gas mixture comprising 4.8% by volume of acrolein, 7% by volume of oxygen, 10% by volume of steam and 78.2% by volume of nitrogen (at a space velocity of the catalyst load of 85 l (S.T.P.) of acrolein/l of catalyst load·h) through the loaded catalyst tube, an acrolein conversion of 97 mol % is achieved (l of catalyst load does not include the volumes inside the catalyst tube where pure preliminary or subsequent beds of inert material are present, only the bed volumes which contain catalyst moldings (if required, diluted with inert material).
Such catalyst load are particularly suitable for higher acrolein velocities (e.g. ≧135 l to 350 l (S.T.P.) per l per h or more).

Comparative Example 1

Everything was carried out as in Example 1. However, the stream of gas mixture fed to the rotary tube contained from the outset (i.e. on the way to the material temperature of 100°

C. or 300° C.) 95 m³(S.T.P.)/h composed of base load of nitrogen (20) and gases liberated in the rotary tube and 70 m³(S.T.P.)/h of recirculated gas, but from the outset 15 m³(S.T.P.)/h of air (splitter (21)) and thus 1.5% by volume of molecular oxygen.

The salt bath temperature required in the testing of the coated catalyst for an acrolein conversion of 99.3 mol % was 268° C. and the selectivity of the acrylic acid formation was only 94.2 mol %.

Comparative Example 2

Everything was carried out as in Example 1. During the entire duration of the thermal treatment, however, the gas stream fed to the rotary tube contained no air at all (instead of the air stream according to the example, the corresponding nitrogen stream was always fed via the splitter).

The salt bath temperature required in the testing of the coated catalyst for an acrolein conversion of 99.3 mol % was 279° C. and the selectivity of the acrylic acid formation was only 91.0 mol %.

Example 2

Everything was carried out as in Example 1. The shaping of the multimetal oxide active material was effected, however, as follows:

70 kg of annular supports (7.1 mm external diameter, 3.2 mm length, 4.0 mm internal diameter, steatite of type C220 from CeramTec, having a surface roughness $R_z$ of 45 μm and a total pore volume, based on the volume of the support, of ≦1% by volume) were introduced into a coating pan (angle of inclination 90°; Hicoater from Lödige, Germany) having an internal volume of 200 l. The coating pan was then caused to rotate at 16 rpm. From 3.8 to 4.2 liters of an aqueous solution of 75% by weight of water and 25% by weight of glycerol were sprayed onto the supports via a nozzle in the course of 25 minutes. At the same time, 18.1 kg of the milled multimetal oxide active material were continuously metered via a vibrating channel outside the spray cone of the atomizer nozzle in the same period. During the coating, the powder fed in was completely taken up onto the surface of the support, and agglomeration of the finely divided oxidic active material was not observed. After the end of the addition of active material powder and water, hot air (about 400 m³/h) was blown into the coating pan at a rotation speed of 2 rpm for 40 minutes (alternatively from 15 to 60 minutes) at 100° C. (alternatively from 80 to 120° C.). Annular coated catalysts whose proportion of anoxidic active material was 20% by weight, based on the total material, were obtained. The coat thickness was 170±50 μm, considered both over the surface of one support and over the surface of different supports.

The testing of the coated catalysts was effected as in Example 1. The results obtained corresponded to the results achieved in Example 1.

Figure 4:
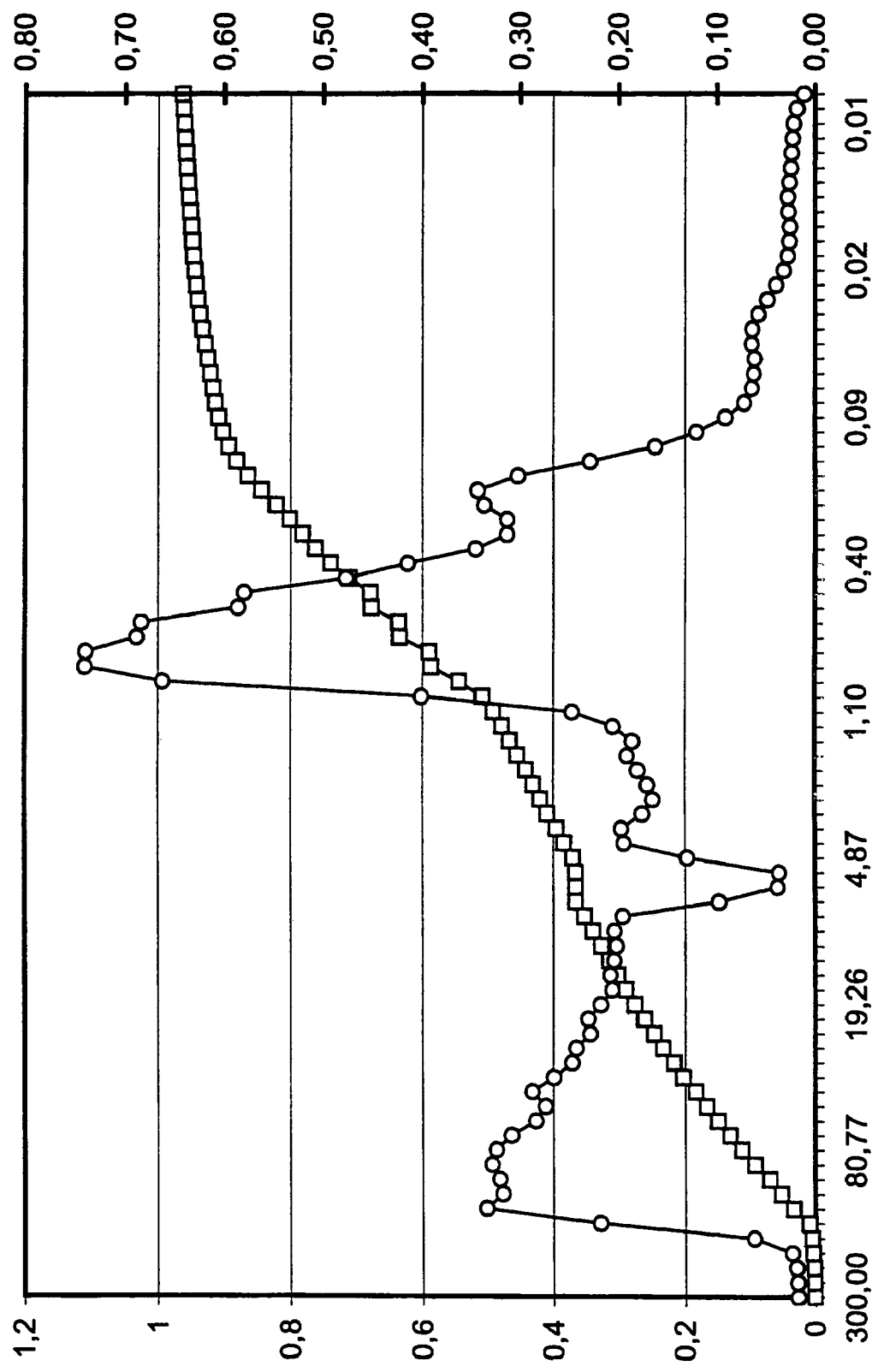
FIG. 4 shows the pore distribution of the milled active material powder before its shaping (its specific surface area was 21 m$^2$/g). The pore diameter in μm is plotted along the abscissa (logarithmic scale).

FIG. 4 also shows the pore distribution of the milled active material powder before its shaping (its specific surface area was 21 m²/g). The pore diameter in μm is plotted along the abscissa (logarithmic scale).

The logarithm of the differential contribution in ml/g of the respective pore diameter to the total pore volume is plotted along the right ordinate (curve O). The maximum has the pore diameter with the greatest contribution to the total pore volume. The integral over the individual contributions of the individual pore diameters to the total pore volume is plotted along the left ordinate, in ml/g (curve □). The end point is the total pore volume (all data in this document on determinations of total pore volumes and of diameter distributions over these total pore volume are, unless stated otherwise, based on determinations by the mercury porosimetry method using the Auto Pore 9220 apparatus from Micromeritics GmbH, 4040 Neuβ, Germany (bandwidth 30 Å to 0.3 mm); all data in this document on determinations of specific surface areas or of micropore volumes are based on determinations according to DIN 66131 (determination of the specific surface area of solids by gas adsorption ($N_2$) according to Brunauer-Emmet-Teller (BET)).

Figure 5:
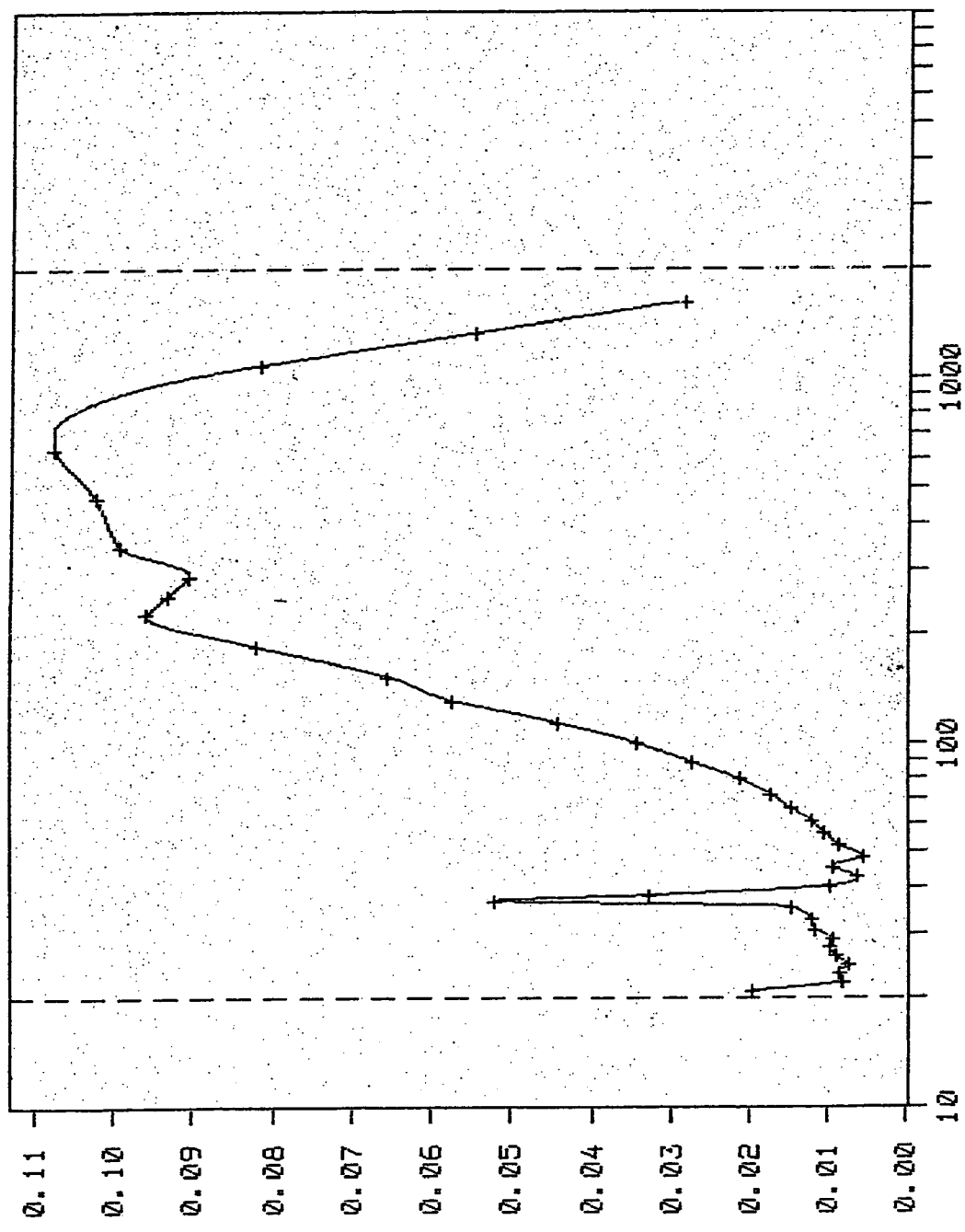
FIG. 5 shows the individual contributions of the individual pore diameters (abscissa, in Angstrom, logarithmic scale) in the micropore region to the total pore volume for the active material powder before its shaping, in ml/g (ordinate).

FIG. 5 shows the individual contributions of the individual pore diameters (abscissa, in Angström, logarithmic scale) in the micropore region to the total pore volume for the active material powder before its shaping, in ml/g (ordinate).

Figure 6:
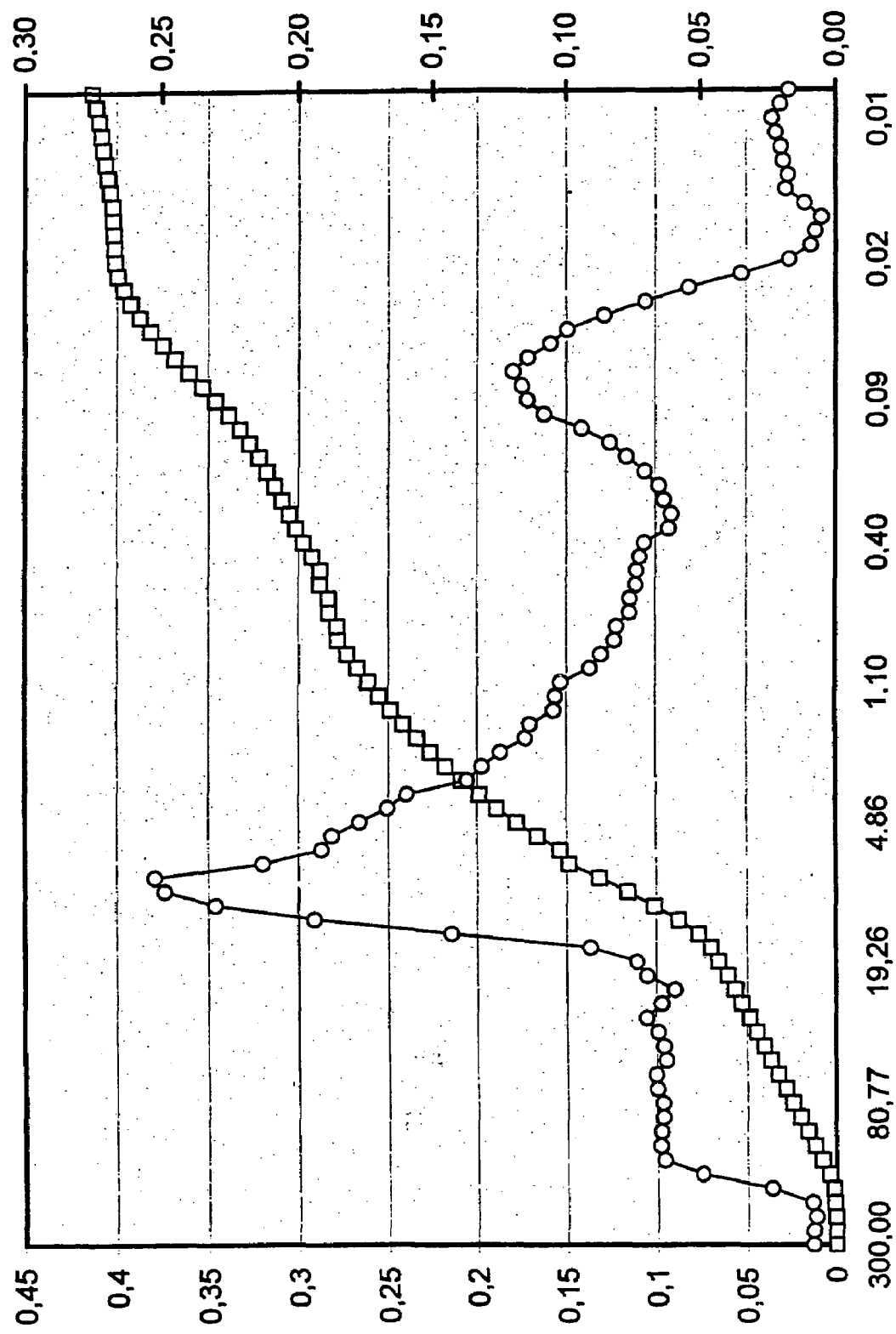
FIG. 6 shows the same as FIG. 4, but for multimetal oxide active material (its specific surface area was 24.8 m$^2$/g) subsequently detached from the annular coated catalyst by scratching off mechanically.

FIG. 6 shows the same as FIG. 4, but for multimetal oxide active material (its specific surface area was 24.8 m²/g) subsequently detached from the annular coated catalyst by scratching off mechanically.

Figure 7:
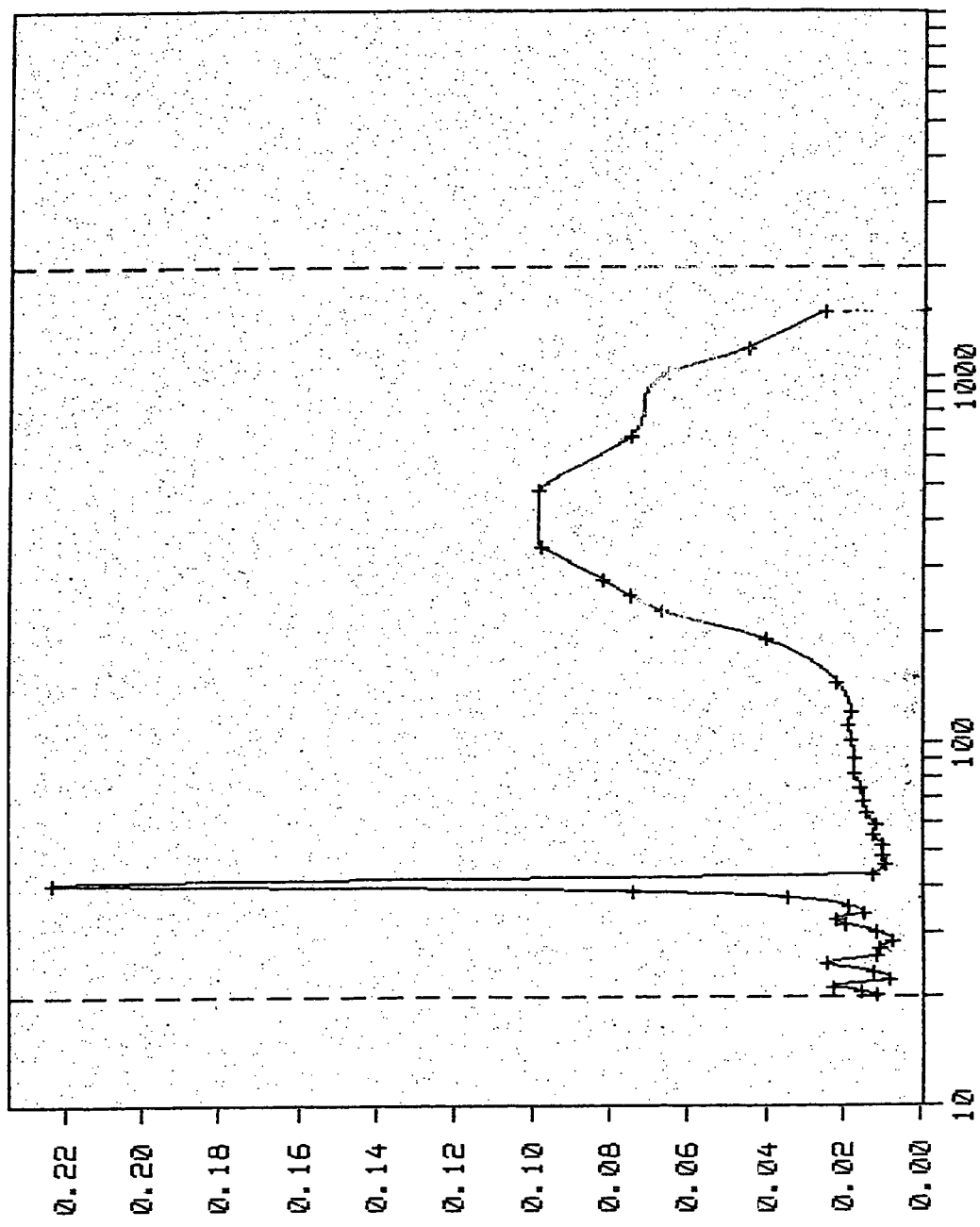
FIG. 7 shows the same as FIG. 5, but for multimetal oxide active material subsequently detached from the annular coated catalyst by scratching off mechanically.

FIG. 7 shows the same as FIG. 5, but for multimetal oxide active material subsequently detached from the annular coated catalyst by scratching off mechanically.

Example 3

Everything was carried out as in Example 1. The shaping of the multimetal oxide active material was effected, however, as follows:

70 kg of spherical support (diameter 4 to 5 mm; steatite of type C220 from CeramTec, having a surface roughness $R_z$, of 45 μm and a total pore volume, based on the volume of the support, of ≦1% by volume) were introduced into a coating pan (angle of inclination 90°; Hicoater from Lödige, Germany) having an internal volume of 200 l. The coating pan was then caused to rotate at 16 rpm. From 2.8 to 3.3 liters of water were sprayed onto the support via a nozzle in the course of 25 minutes. At the same time, 14.8 kg of the milled multimetal oxide active material were continuously metered via a vibrating channel outside the spray cone of the atomizer nozzle in the same period. During the coating, the powder fed in was completely taken up onto the surface of the supports, and agglomeration of the finely divided oxidic active material was not observed. After the end of the addition of powder and water, hot air (about 400 m³/h) was blown into the coating pan at a rotational speed of 2 rpm for 40 minutes (alternatively from 15 to 60 minutes) at 100° C. (alternatively from 80 to 120° C.). Spherical coated catalysts whose proportion of oxidic active material was 17% by weight, based on the total material, were obtained. The coat thickness was 160±50 μm, considered both over the surface of one support and over the surface of different supports.

Figure 8:
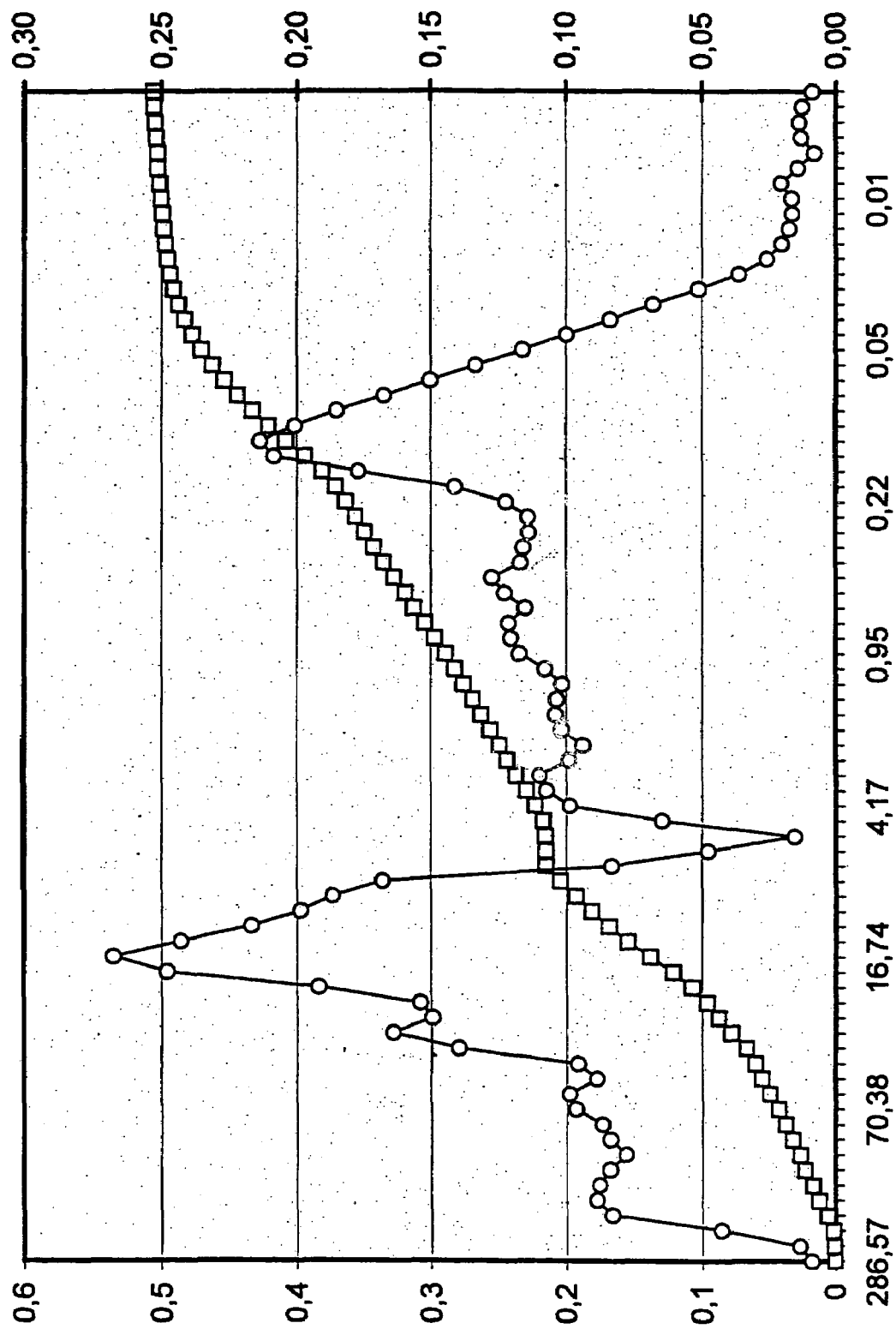
FIG. 8 shows the analog of FIG. 6 (the specific surface area of the scratched-off multimetal oxide active material was 20.3 m$^2$/g).

FIG. 8 shows the analog of FIG. 6 (the specific surface area of the scratched-off multimetal oxide active material was 20.3 m²/g).

Figure 9:
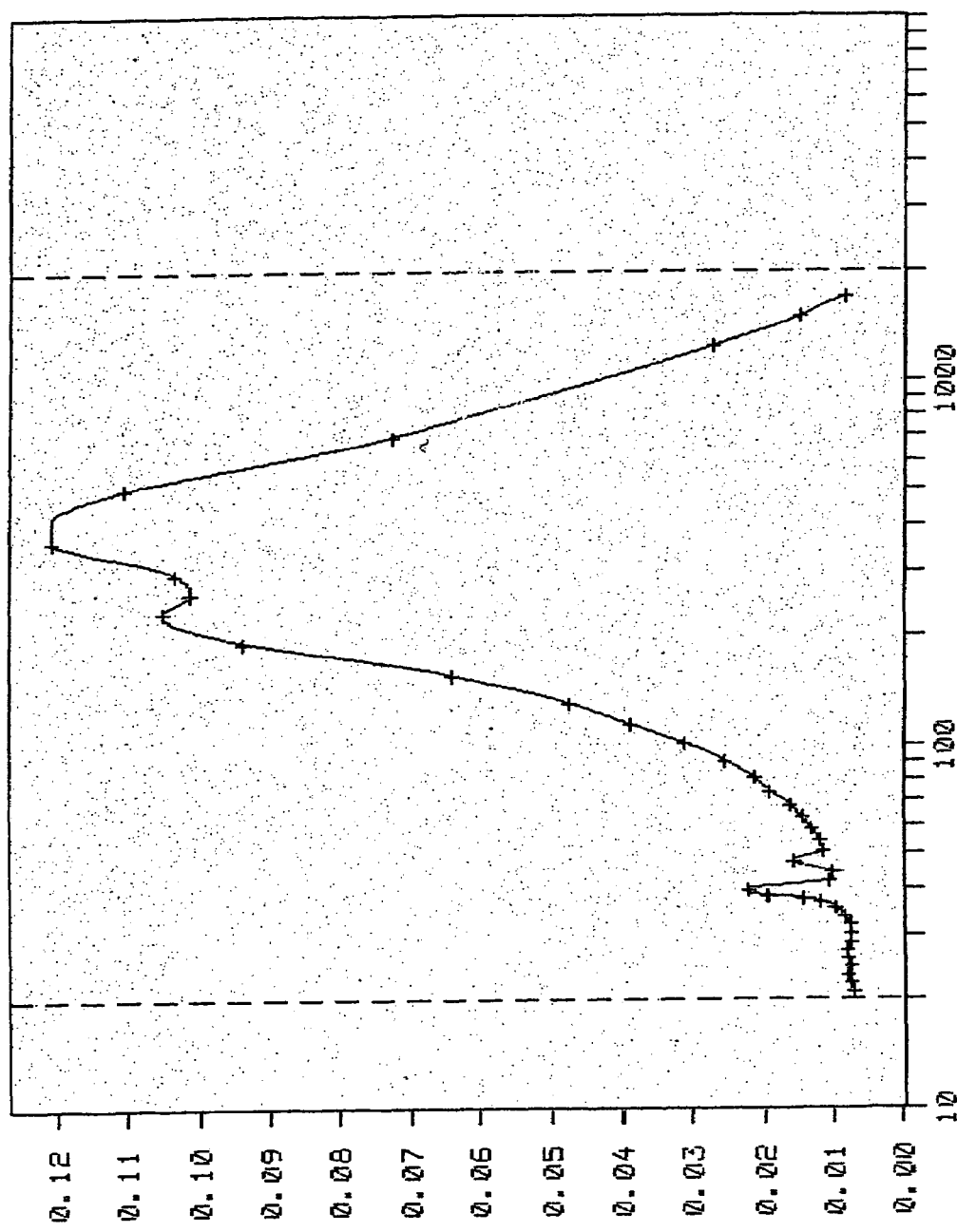
FIG. 9 shows the analog of FIG. 7.

FIG. 9 shows the analog of FIG. 7.

The testing of the spherical coated catalyst was effected as described in Example 1 for the annular coated catalyst.

All coated catalysts prepared in this document by way of example are particularly suitable for acrolein partial oxidation at high acrolein spin velocities of the catalyst load (e.g. ≧135 to 350 l (S.T.P.) per l per h).

We claim:

1. A process for the preparation of a catalytically active multimetal oxide comprising material which comprises at least one of the elements Nb and W, and the elements Mo, V and Cu, wherein the molar fraction of the element Mo, based on the total amount of all elements other than oxygen in the catalytically active multimetal oxide comprising material, is from 20 to 80 mol %, wherein the molar ratio of Mo to V, Mo/V, is from 15:1 to 1:1, wherein the corresponding molar ratio Mo/Cu is from 30:1 to 1:3 and the corresponding molar ratio Mo/(total amount of W and Nb) is from 80:1 to 1:4, the process comprising preparing an intimate dry blend comprising ammonium ions from starting compounds that comprise the elemental constituents of the multimetal oxide comprising material, other than oxygen, as components; and thermally treating the intimate dry blend at elevated temperatures in an atmosphere A having a low content of molecular oxygen, so that at least a portion of the ammonium ions contained in the intimate dry blend are decomposed at $\geq 160°$ C. with liberation of ammonia, wherein the thermal treatment is carried out as follows:

heating the intimate dry blend at a heating rate of $\leq 10°$ C./min to a decomposition temperature in a decomposition temperature range of from 240° C. to 360° C., and then keeping the temperature in the decomposition range until at least 90 mol % of the total amount $M^A$ of ammonia liberated altogether in the entire course of the thermal treatment of the intimate dry blend from the intimate dry blend at above 160° C. has been liberated;

reducing, to less than or equal to 0.5% by volume, the content of molecular oxygen in the atmosphere A in which the thermal treatment of the intimate dry blend takes place no later than when the intimate dry blend has reached 230° C., and maintaining the reduced oxygen content until at least 20 mol % of the total amount $M^A$ of ammonia liberated altogether in the entire course of the thermal treatment has been liberated;

taking the intimate blend out of the decomposition temperature range, at a rate of $\leq 10°$ C./min, and into a calcination temperature range of from 380 to 450° C. no earlier than when $\geq 70$ mol % of the total amount of $M^A$ of ammonia liberated altogether in the entire course of the thermal treatment has been liberated increasing the content of molecular oxygen in the atmosphere A to >0.5 to 4% by volume no later than when 98 mol % of the total amount $M^A$ of ammonia liberated altogether in the entire course of the thermal treatment has been liberated and calcining the intimate dry blend at this increased oxygen content of the atmosphere A in the calcination temperature range.

2. The process as claimed in claim 1, wherein the content of ammonium ions in the intimate dry blend, prior to the thermally treating step, is $\geq 5$ mol %, based on the total molar content of elemental constituents of the subsequent catalytically active multimetal oxide comprising material, other than oxygen, in the intimate dry blend.

3. The process as claimed in claim 1 or 2, wherein the temperature rate at which the intimate dry blend is heated to the decomposition temperature is $\leq 5°$ C./min.

4. The process of claim 1, wherein the temperature rate at which the intimate dry blend is heated to the decomposition temperature is $\leq 3°$ C./min.

5. The process of claim 1, wherein the decomposition temperature range is from 300 to 350° C.

6. The process of claim 1, wherein the intimate dry blend is kept in the decomposition temperature range until at least 95 mol % of the total amount $M^A$ of ammonia liberated altogether in the entire course of the thermal treatment of the intimate dry blend from the intimate dry blend at above 160° C. has been liberated.

7. The process of claim 1, wherein the content of molecular oxygen in the atmosphere A is $\leq 0.3\%$ by volume no later than when the intimate dry blend has reached 230° C.

8. The process of claim 1, wherein the content of molecular oxygen in the atmosphere A is increased to >0.5 to 4% by volume before 80 mol % of the total amount $M^A$ of ammonia liberated altogether in the entire course of the thermal treatment has been liberated.

9. The process of claim 1, wherein the content of molecular oxygen in the atmosphere A is increased to 0.6 to 4% by volume no later than when 98 mol % of the total amount $M^A$ of ammonia liberated altogether in the entire course of the thermal treatment has been liberated.

10. The process of claim 1, wherein the content of molecular oxygen in the atmosphere A is increased to 1 to 3% by volume no later than when 98 mol % of the total amount $M^A$ of ammonia liberated altogether in the entire course of the thermal treatment has been liberated.

11. The process of claim 1, wherein the calcination temperature range is from 380 to 430° C.

12. The process of claim 1, wherein, after calcination is complete, the intimate dry blend is cooled to $\leq 100°$ C. in the course of a period of $\leq 5$ hours.

13. The process as claimed in claim 12, wherein the cooling is effected to at least 350° C. in an atmosphere A whose content of molecular oxygen is $\leq 5\%$ by volume.

14. The process of claim 1, wherein the ammonia content of the atmosphere A passes through a maximum which is $\leq 10\%$ by volume in the course of the thermal treatment.

15. The process as claimed in claim 14, wherein the atmosphere A reaches its maximum ammonia content before the intimate dry blend has reached the calcination temperature range.

16. The process of claim 1, wherein the catalytically active multimetal oxide comprising material satisfies the stoichiometry I $$Mo_{12}V_aX^1_bX^2_cX^3_dX^4_eX^5_fX^6_gO_n \qquad (I),$$

wherein:

$X^1$ is W, Nb, Ta, Cr and/or Ce, $X^2$ is Cu, Ni, Co, Fe, Mn and/or Zn, $X^3$ is Sb and/or Bi, $X^4$ is one or more alkali metals, $X^5$ is one or more alkaline earth metals, $X^6$ is Si, Al, Ti and/or Zr, a is from 1 to 6, b is from 0.2 to 4, c is from 0.5 to 18, d is from 0 to 40, e is from 0 to 2, f is from 0 to 4, g is from 0 to 40 and n is a number which is determined by the valency and frequency of the elements other than oxygen in I.

17. The process of claim 1, wherein the catalytically active multimetal oxide comprising material is one of the formula III $[A]_p[B]_q[C]_r$ (III) wherein:

A is $Mo_{12}V_aX^1_bX^2_cX^3_dX^4_eX^5_fX^6_gO_x$,

B is $X^7_1Cu_hH_iO_y$,

C is $X^8_1Sb_jH_kO_z$, $X^1$ is W, Nb, Ta, Cr and/or Ce, $X^2$ is Cu, Ni, Co, Fe, Mn and/or Zn, $X^3$ is Sb and/or Bi, $X^4$ is Li, Na, K, Rb, Cs and/or H, $X^5$ is Mg, Ca, Sr and/or Ba,
$X^6$ is Si, Al, Ti and/or Zr,
$X^7$ is Mo, W, V Nb and/or Ta,
$X^8$ is Cu, Ni, Zn, Co, Fe, Cd, Mn, Mg, Co, Sr and/or Ba,
a is from 1 to 8,
b is from 0.2 to 5,
c is from 0 to 23,
d is from 0 to 50,
e is from 0 to 2,
f is from 0 to 5,
g is from 0 to 50,
h is from 0.3 to 2.5
i is from 0 to 2,
j is from 0.1 to 50,
k is from 0 to 50,
x, y and z are numbers which are determined by the valency and frequency of the elements other than oxygen in A, B and C,
p and q are positive numbers and
r is 0 or a positive number, the ratio p/(q+r) being from 20:1 to 1:20 and, where r is a positive number, the ratio q/r being from 20:1 to 1:20,
which contains the moiety $[A]_p$ in the form of three-dimensional regions A having the chemical composition A: $Mo_{12}V_aX^1_bX^2_cX^3_dX^4_eX^4_fX^6_gO_x$,
the moiety $[B]_q$ in the form of three-dimensional regions B having the chemical composition
B: $X^7_1Cu_hH_iO_y$, and
the optional moiety $[C]_r$ in the form of three-dimensional regions C having the chemical composition
C: $X^8_1Sb_jH_kO_z$,
the regions A, B and, if desired, C being distributed relative to one another as in a mixture of finely divided A, finely divided B and, if desired, finely divided C.

18. The process of claim 1, wherein the thermal treatment is carried out in a rotary tube furnace through which a gas stream flows.

19. The process as claimed in claim 18, wherein the rotary tube furnace is operated batchwise.

20. The process as claimed in claim 18 or 19, wherein at least a portion of the gas stream running through the rotary tube is circulated.

21. The process as claimed in claim 18 or 19, wherein the pressure of the gas stream flowing through the rotary tube on leaving the rotary tube is below the ambient pressure of the rotary tube.

* * * * *